United States Patent
Watanabe et al.

(10) Patent No.: US 10,730,830 B2
(45) Date of Patent: Aug. 4, 2020

(54) TETRAHYDRONAPHTHALENE DERIVATIVE

(71) Applicant: ONO PHARMACEUTICAL CO., LTD., Osaka (JP)

(72) Inventors: Toshihide Watanabe, Osaka (JP); Kensuke Kusumi, Osaka (JP); Yuichi Inagaki, Ibaraki (JP)

(73) Assignee: ONO PHARMACEUTICAL CO., LTD., Osaka (JP)

(*) Notice: Subject to any disclaimer, the term of this patent is extended or adjusted under 35 U.S.C. 154(b) by 0 days.

(21) Appl. No.: 16/073,620

(22) PCT Filed: Jan. 27, 2017

(86) PCT No.: PCT/JP2017/002911
§ 371 (c)(1),
(2) Date: Jul. 30, 2018

(87) PCT Pub. No.: WO2017/131149
PCT Pub. Date: Aug. 3, 2017

(65) Prior Publication Data
US 2019/0031605 A1    Jan. 31, 2019

(30) Foreign Application Priority Data

Jan. 29, 2016   (JP) ................ 2016-015064

(51) Int. Cl.
| | | |
|---|---|---|
| *C07D 205/04* | (2006.01) | |
| *C07D 223/16* | (2006.01) | |
| *C07D 405/12* | (2006.01) | |
| *C07D 207/16* | (2006.01) | |
| *A61K 31/472* | (2006.01) | |
| *C07D 217/16* | (2006.01) | |
| *C07C 229/46* | (2006.01) | |
| *A61K 31/55* | (2006.01) | |
| *C07D 217/04* | (2006.01) | |
| *C07D 223/06* | (2006.01) | |
| *A61K 31/402* | (2006.01) | |
| *A61K 31/397* | (2006.01) | |
| *A61K 31/197* | (2006.01) | |
| *C07C 33/30* | (2006.01) | |
| *C07C 33/34* | (2006.01) | |
| *C07C 43/23* | (2006.01) | |
| *C07C 49/84* | (2006.01) | |
| *C07C 69/612* | (2006.01) | |
| *C07C 229/42* | (2006.01) | |
| *C07C 409/38* | (2006.01) | |

(Continued)

(52) U.S. Cl.
CPC .......... *C07D 205/04* (2013.01); *A61K 31/197* (2013.01); *A61K 31/397* (2013.01); *A61K 31/402* (2013.01); *A61K 31/472* (2013.01); *A61K 31/55* (2013.01); *C07C 33/30* (2013.01); *C07C 33/34* (2013.01); *C07C 43/23* (2013.01); *C07C 49/84* (2013.01); *C07C 69/612* (2013.01); *C07C 229/42* (2013.01); *C07C 229/46* (2013.01); *C07C 409/38* (2013.01); *C07D 207/16* (2013.01); *C07D 217/04* (2013.01); *C07D 217/16* (2013.01); *C07D 217/26* (2013.01); *C07D 223/06* (2013.01); *C07D 223/16* (2013.01); *C07D 403/12* (2013.01); *C07D 405/12* (2013.01); *C07D 417/12* (2013.01); *C07C 2601/02* (2017.05); *C07C 2602/08* (2017.05); *C07C 2602/10* (2017.05)

(58) Field of Classification Search
None
See application file for complete search history.

(56) References Cited

U.S. PATENT DOCUMENTS 5,912,342 A    6/1999  Heinonen et al.
8,198,454 B2*  6/2012  Nakamura ............ C07C 233/59
                                                    546/256

(Continued)

FOREIGN PATENT DOCUMENTS

EP    0 026 848 A1    4/1981
EP    0 035 868 A1    9/1981

(Continued)

OTHER PUBLICATIONS

Chemical Abstract Registry No. 1539002-93-1 indexed in the Registry File on STN CAS Online Feb. 7, 2014.*

(Continued)

Primary Examiner — Joseph R Kosack
(74) Attorney, Agent, or Firm — Sughrue Mion, PLLC

(57) ABSTRACT

A compound of general formula (I-1):

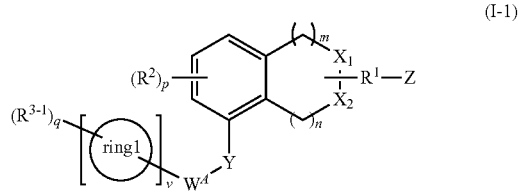

wherein the symbols are defined in the specification, has a selective $S1P_5$ receptor binding activity and modulates the function of an $S1P_5$ receptor, and can therefore be a therapeutic agent for a $S1P_5$-mediated disease, for example, neurodegenerative diseases such as schizophrenia, Binswanger's disease and the like.

17 Claims, No Drawings

(51) Int. Cl.
C07D 217/26 (2006.01)
C07D 403/12 (2006.01)
C07D 417/12 (2006.01)

(56) References Cited

U.S. PATENT DOCUMENTS

| | | | |
|---|---|---|---|
| 2004/0029859 | A1 | 2/2004 | Blagg et al. |
| 2004/0110748 | A1 | 6/2004 | Beavers et al. |
| 2007/0037846 | A1 | 2/2007 | Fretz et al. |
| 2007/0173487 | A1 | 7/2007 | Saha et al. |
| 2009/0324581 | A1 | 12/2009 | Machinaga et al. |
| 2010/0240671 | A1 | 9/2010 | Zhuo et al. |
| 2012/0101083 | A1 | 4/2012 | Bailey et al. |
| 2013/0131035 | A1 | 5/2013 | Bregman et al. |
| 2015/0203493 | A1 | 7/2015 | Guckian et al. |
| 2015/0376173 | A1 | 12/2015 | Paek et al. |

FOREIGN PATENT DOCUMENTS

| | | |
|---|---|---|
| EP | 0 270 947 A2 | 6/1988 |
| JP | 2004-532834 A | 10/2004 |
| JP | 2005-532275 A | 10/2005 |
| JP | 2007-506661 A | 3/2007 |
| JP | 2009-114107 A | 5/2009 |
| JP | 2009-520688 A | 5/2009 |
| JP | 2012-530108 A | 11/2012 |
| JP | 2013-519732 A | 5/2013 |
| WO | 90/15047 A1 | 12/1990 |
| WO | 03011862 A1 | 2/2003 |
| WO | 2006/085149 A2 | 8/2006 |
| WO | 2007/129745 A1 | 11/2007 |
| WO | 2010/146105 A1 | 12/2010 |
| WO | 2014/129796 A1 | 8/2014 |
| WO | 2016/108045 A2 | 7/2016 |

OTHER PUBLICATIONS

Chemical Abstract Registry No. 1543023-50-2 indexed in the Registry File on STN CAS Online Feb. 13, 2014.*
Bigaud et al., Second generation S1p pathway modulators: Research strategies and clinical development. Biochimica et Biophysica Acta 2014, 1841, 745-758.*
Chafer, S., Kolkhof, P. Failure is an option: learning from unsuccessful proof-of-concept trials. Drug Discovery Today. Nov. 2008, 13, 913-916.*
Honig, H., Pullman, W. From bench to clinic and back: Perspective on the 1st IQPC Translational Research conference. Journal of Translational Medicine. Dec. 2004, 2, 44.*
Ito et al., A medium-term rat liver bioassay for rapid in vivo detection of carcinogenic potential of chemicals. Cancer Science, 2003, 94, 3-8.*
Schafer, S., Kolkhof, P. Failure is an option: learning from unsuccessful proof-of-concept trials. Drug Discovery Today. Nov. 2008, 13, 913-916.*
Chemical Abstract Registry No. 1500322-42-8, indexed in the Registry File on STN CAS Online Dec. 22, 2013.*
C. Jaillard et al. "Edg8/S1P5: An Oligodendroglial Receptor with Dual Function on Process Retraction and Cell Survival" The Journal of Neuroscience, vol. 25, No. 6, Feb. 9, 2005 (pp. 1459-1469).
Alexander S. Novgorodov et al. "Activation of sphingosine-1-phosphate receptor S1P5 inhibits oligodendrocyte progenitor migration" The FASEB Journal • Research Communication vol. 21, No. 7, Mar. 2017 (pp. 1503-1514).
Thierry Walzer et al. "Natural killer cell trafficking in vivo requires a dedicated sphingosine 1-phosphate receptor" Nature Immunology, vol. 8, No. 12, Dec. 2007 (pp. 1337-1344).
Emille Debien et al. "S1PR5 is pivotal for the homeostasis of patrolling monocytes" European Journal Immunology, vol. 43, 2013 (pp. 1667-1675).
Richard N. Hanna et al. "Patrolling monocytes control tumor metastasis to the lung" Cancer Immunology, vol. 350, Issue 6263, Nov. 20, 2015, (pp. 985-990).
International Search Report (PCT/ISA/210), issued by International Searching Authority in corresponding International Application No. PCT/JP2017/002911, dated Apr. 18, 2017.
Written Opinion (PCT/ISA/237) issued by the International Searching Authority in corresponding International Application No. PCT/JP2017/002911, dated Apr. 18, 2017.
John Skidmore et al. "Optimization of Sphingosine-1-phosphate-1 Receptor Agonists: Effects of Acidic, Basic, and Zwitterionic Chemotypes on Pharmacokinetic and Pharmacodynamic Profiles" Journal of Medicinal Chemistry, vol. 57, No. 24, 2014 (pp. 10424-10442).
McDermed et al., "Synthesis and Pharmacology of Some 2-Aminotetralins, Dopamine Receptor Agonists", Journal of Medicinal Chemistry, Jan. 1975, pp. 362-367, 6 pages total, XP002067369.
Emerit et al., "Irreversible Blockade of Central 5-HT1A Receptor Binding Sites by the Photoaffinity Probe 8-Methoxy-3'-NAP-Amino-PAT", European Journal of Pharmacology, vol. 127, Aug. 1986, pp. 67-81, 15 pages total, XP023750423.
Communication dated Dec. 11, 2019 issued by the European Intellectual Property Office in counterpart European Application No. 17744379.3.
European Patent Office, Communication dated Apr. 23, 2020 issued in European Application No. 17744379.3.
Shoji Kamiya et al. "A Novel Series of Thromboxane A□ Synthetase Inhibitors with Free Radical Scavenging and Anti-peroxidative Activities" Chemical and Pharmaceutical Bulletin, vol. 49, No. 5, May 1, 2001, (pp. 563-571) XP002973344.

* cited by examiner

TETRAHYDRONAPHTHALENE DERIVATIVE

TECHNICAL FIELD

The present invention relates to a compound represented by general formula (I-1):

[Chemical Formula 1]

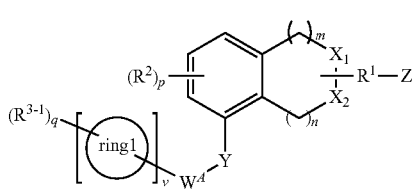

(wherein, all the symbols have the same meanings as described below), or a pharmaceutically acceptable salt thereof (hereinafter occasionally abbreviated as the compound of the present invention).

BACKGROUND ART

Sphingosine-1-phosphate [(2S,3R,4E)-2-amino-3-hydroxyoctadec-4-enyl-1-phosphate; hereinafter occasionally abbreviated as S1P] is a lipid which is synthesized by metabolic turnover of sphingolipids in cells and by the extracellular action of a secreted sphingosine kinase. It is proposed that sphingosine-1-phosphate acts as an intercellular communication mediator as well as an intracellular second messenger.

Among S1P receptors, with regard to $S1P_5$ (EDG-8) receptor, it is known that $S1P_5$ (EDG-8) receptor is highly expressed in oligodendrocytes (oligodendroglia) and oligodendrocyte progenitor cells (see Non Patent Literatures 1 and 2). Oligodendrocytes are a kind of glial cells which form the myelin sheaths (myelin) by binding to the axons of nerve cells. Accordingly, it is considered that a compound which has an $S1P_5$ receptor binding activity, and can mediate the function of an $S1P_5$ receptor, is useful for treating neurodegenerative disease such as schizophrenia because the compound promotes the regeneration of myelin which has disappeared (demyelination) in nerve cells.

In addition, it is known that $S1P_5$ receptor is highly expressed also in natural killer (NK) cells and it is revealed that the migration of NK cells is induced by the activation of $S1P_5$ receptor (see Non Patent Literature 3).

Further, $S1P_5$ receptor is highly expressed in patrolling monocytes which are known to be involved in the tumor immunity, and therefore, there is a possibility that the activation of the tumor immunity is induced by the activation of $S1P_5$ receptor (see Non Patent Literatures 4 and 5).

Incidentally, as compounds of prior arts to the present invention, the following compounds are known.

It is disclosed that a compound represented by general formula (a):

[Chemical Formula 2]

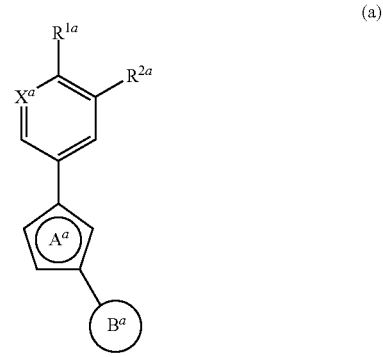

(wherein, $X^a$ represents CH or N, $R^{1a}$ represents a C3-6 cycloalkyl group which has a fluorine substituent(s), $R^{2a}$ represents a hydrogen atom, a halogen atom, a cyano group or a trifluoromethyl group, $A^a$ represents a 5-membered heterocyclic ring which is chosen between thiazole, thiadiazole or the like, $B^a$ represents bicyclic ring which is chosen between a substituent as shown below;

[Chemical Formula 3]

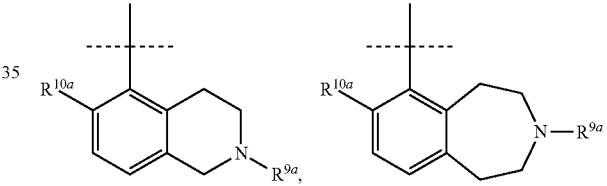

(wherein, $R^{9a}$ represents a C1-4 alkyl group which has at lease one hydroxy group substituent, $R^{10a}$ represents a hydrogen atom or a C1-3 alkyl group which may be substituted with a halogen atom) (provided that the definition of each of groups is excerpted)) has an $S1P_1$ agonist activity (see Patent Literature 1).

Also, it is known that a compound represented by general formula (b):

[Chemical Formula 4]

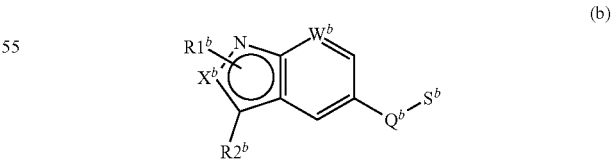

(wherein, $X^b$ represents C or N, $R^{1b}$ represents H or an alkyl group which may have a substituent(s), $R^{2b}$ represents H, an alkyl group which may have a substituent(s), a halogen atom or the like, $W^b$ represents C, N or a C-alkoxy group, $Q^b$ represents $CH_2O$ or the like, $S^b$ represents a substituent as shown below;

[Chemical Formula 5]

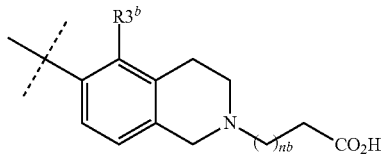

(wherein, $R3^b$ represents H, an alkyl group, a halogen atom or the like, nb represents 0 to 3) (provided that the definition of each of groups is excerpted)) has an S1P agonist activity (see Patent Literature 2).

None of prior arts discloses or suggests that the compound of the present invention has a selective $S1P_5$ binding activity and modulates the function of an $S1P_5$ receptor.

CITATIONS LISTS

Patent Literatures

Patent Literature 1: WO 2010/146105 A
Patent Literature 2: WO 2014/129796 A

Non Patent Literatures

Non Patent Literature 1: The Journal of Neuroscience, Vol. 25, No. 6, pages 1459-1469, 2005
Non Patent Literature 2: The FASEB Journal, Vol. 21, pages 1503-1514, 2007
Non Patent Literature 3: Nature Immunology, Vol. 8, No. 12, pages 1337-1344, 2007
Non Patent Literature 4: European Journal of Immunology, Vol. 43, pages 1667-1675, 2013
Non Patent Literature 5: Science, Vol. 350, No. 6263, pages 985-990, 2015

SUMMARY OF INVENTION

Technical Problems

An object of the present invention is to provide a compound which has a selective $S1P_5$ receptor binding activity and modulates the function of an $S1P_5$ receptor.

Solutions to Problems

The present inventors have carried out intensive studies to find out a compound which has improved affinity to an $S1P_5$ receptor in order to achieve the above-described object. As a result, the present inventors have found surprisingly that with regard to a compound of the present invention has a selective $S1P_5$ receptor binding activity and modulates the function of an $S1P_5$ receptor, and have completed the present invention.

In other words, the present invention relates to the followings:

[1] a compound represented by general formula (I-1):

[Chemical Formula 6]

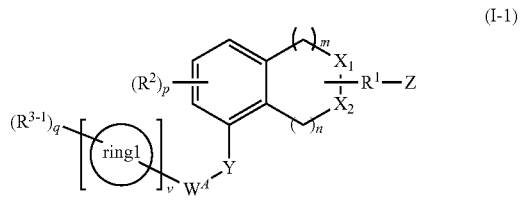

(I-1)

[wherein, $X^1$ and $X^2$ each represent independently a $CH_2$ or an NH, provided that $X^1$ and $X^2$ are not represent NH at the same time,
Y represents (1) —$CH_2$—, (2) —NH—, (3) —S— or (4) —O—,
$W^A$ represents (1) a C1-12 alkylene group, (2) a C2-12 alkenylene group, (3) a C2-12 alkynylene group, (4) —C1-12 alkylene-O—, (5) —C2-12 alkenylene-O—, (6) —C2-12 alkynylene-O—, (7) —C1-12 alkylene-ring2-, (8) —C2-12 alkenylene-ring2- or (9) —C2-12 alkynylene-ring2-, wherein, an alkylene group, an alkenylene group and an alkynylene group may be substituted with one to five halogen atoms,
$R^1$ represents (1) -L-, (2) -L-ring3- or (3) -L-$NR^{13}$,
$R^2$ represents (1) a halogen atom, (2) a C1-4 alkyl group, (3) a C1-4 haloalkyl group, (4) a C1-4 alkoxy group or (5) a C1-4 haloalkoxy group,
$R^{3-1}$ represents (1) a halogen atom, (2) a C1-4 alkyl group, (3) a C1-4 haloalkyl group, (4) a C1-4 alkoxy group, (5) a C1-4 haloalkoxy group, (6) a nitrile group, (7) —S—C1-4 alkyl group, (8) —S—C1-4 haloalkyl group or (9) an oxo group, provided that the C1-4 alkyl group or the C1-4 haloalkyl group represented by $R^{3-1}$ is branched chain, C1-2 alkyl groups branched from the same carbon atom may be taken together with a carbon atom to which they are bound, to form a C3-4 saturated carbocyclic ring,
$R^{13}$ represents (1) a hydrogen atom or (2) a C1-4 alkyl group,
L represents (1) a bond or (2) a group represented by general formula

[Chemical Formula 7]

(wherein, $R^{11}$ and $R^{12}$ each represent independently a hydrogen atom or a C1-4 alkyl group, or $R^{11}$ and $R^{12}$ may be taken together with a carbon atom to which they are bound, to form a C3-7 carbocyclic ring, and t represents an integer of 1 to 6),
Z represents (1) a carboxyl group which may be substituted with a C1-8 alkyl group, (2) a hydroxy group which may be substituted with a C1-8 alkyl group, (3) a hydroxamic acid group which may be substituted with a C1-8 alkyl group, (4) a sulfonic acid group which may be substituted with a C1-8 alkyl group, (5) a boronic acid group which may be substituted with a C1-8 alkyl group, (6) a carbamoyl group which may be substituted with a C1-8 alkyl group, (7) a sulfamoyl group which may be substituted with a C1-8 alkyl group, (8)

a sulfoximine group which may be substituted with a C1-8 alkyl group or (9) a tetrazolyl group,
ring 1 represents (1) a C3-10 carbocyclic ring or (2) a 3- to 10-membered heterocyclic ring,
ring 2 represents (1) a C3-7 carbocyclic ring or (2) a 3- to 7-membered heterocyclic ring,
ring 3 represents (1) a C3-7 carbocyclic ring which may be substituted with a C1-4 alkyl group or (2) a 3- to 7-membered heterocyclic ring which may be substituted with a C1-4 alkyl group,
m represents an integer of 0 to 2,
n represents an integer of 0 to 2,
p represents an integer of 0 to 3,
q represents an integer of 0 to 5,
v represents an integer of 0 to 1,
when p is 2 or more, a plurality of $R^2$s may be the same or different,
when q is 2 or more, a plurality of $R^{3-1}$s may be the same or different,
when t is 2 or more, a plurality of $R^{11}$s may be the same or different, and
when t is 2 or more, a plurality of $R^{12}$s may be the same or different], or a pharmaceutically acceptable salt thereof;
[2] the compound according to the above [1], represented by general formula (I):

[Chemical Formula 8]

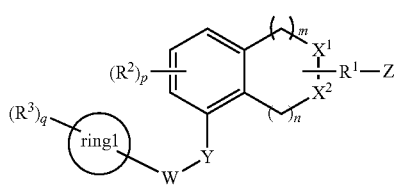

(I)

[wherein, W represents (1) a C1-6 alkylene group, (2) a C2-6 alkenylene group, (3) a C2-6 alkynylene group, (4) a —C1-6 alkylene-O—, (5) a —C2-6 alkenylene-O—, (6) a —C2-6 alkynylene-O— or (7) a —C1-6 alkylene-ring2-,
$R^3$ represents (1) a halogen atom, (2) a C1-4 alkyl group, (3) a C1-4 haloalkyl group, (4) a C1-4 alkoxy group, (5) a C1-4 haloalkoxy group, (6) a nitrile group, (7) a —S—C1-4 alkyl group, or (8) a —S—C1-4 haloalkyl group, provided that the C1-4 alkyl group or the C1-4 haloalkyl group represented by $R^3$ is branched chain, C1-2 alkyl groups branched from the same carbon atom may be taken together with a carbon atom to which they are bound, to form a C3-4 saturated carbocyclic ring,
when q is 2 or more, a plurality of $R^3$s may be the same or different and other symbols have the same meanings as described in the above [1]], or a pharmaceutically acceptable salt thereof;
[3] the compound according to the above [1] or [2], wherein Y is —CH$_2$— or —O—, or a pharmaceutically acceptable salt thereof;
[4] the compound according to any one of the above [1] to [3], wherein ring 1 is a C3-10 carbocyclic ring, or a pharmaceutically acceptable salt thereof;
[5] the compound according to any one of the above [1] to [4], wherein ring 3 is a C3-7 saturated carbocyclic ring which may be substituted with a C1-4 alkyl group, or a 3- to 7-membered saturated heterocyclic ring which may be substituted with a C1-4 alkyl group, or a pharmaceutically acceptable salt thereof;

[6] the compound according to any one of the above [1] to [5], wherein Z is a carboxyl group which may be substituted with a C1-8 alkyl group, or a pharmaceutically acceptable salt thereof;
[7] a pharmaceutical composition comprising the compound represented by general formula (I-1) according to the above [1], or a pharmaceutically acceptable salt thereof;
[8] the pharmaceutical composition according to the above [7], which is an S1P$_5$ binder and/or modulator;
[9] the pharmaceutical composition according to the above [7], which is an agent for preventing and/or treating a S1P$_5$-mediated disease;
[10] the pharmaceutical composition according to the above [9], wherein the S1P$_5$-mediated disease is neurodegenerative disease, autoimmune disease, infection or cancer;
[11] the pharmaceutical composition according to the above [10], wherein the neurodegenerative disease is schizophrenia, Binswanger's disease, multiple sclerosis, neuromyelitis optica, Alzheimer's disease, cognitive impairment, amyotrophic lateral sclerosis or spinocerebellar ataxia;
[12] a method for preventing and/or treating a S1P$_5$-mediated disease, comprising administering to a mammal an effective amount of the compound represented by general formula (I-1) according to the above [1], or a pharmaceutically acceptable salt thereof;
[13] the compound represented by general formula (I-1) according to the above [1], or a pharmaceutically acceptable salt thereof for preventing and/or treating a S1P$_5$-mediated disease;
[14] use of the compound represented by general formula (I-1) according to the above [1], or a pharmaceutically acceptable salt thereof for the manufacture of an agent for preventing and/or treating a S1P$_5$-mediated disease; and the like.

Advantageous Effects of Invention

The compound of the present invention has a selective S1P$_5$ receptor binding activity and modulates the function of an S1P$_5$ receptor, and therefore, the compound of the present invention is useful for treating S1P$_5$-mediated disease, for example, neurodegenerative disease, autoimmune disease, infection and cancer.

DESCRIPTION OF EMBODIMENTS

The present invention will be described in details hereinbelow.
In the present invention, a halogen atom includes a fluorine atom, a chlorine atom, a bromine atom and an iodine atom.
In the present invention, a C1-8 alkyl group includes a linear or branched C1-8 alkyl group. Examples of the C1-8 alkyl group include methyl, ethyl, propyl, butyl, pentyl, hexyl, heptyl, octyl, isopropyl, isobutyl, sec-butyl, tert-butyl, 1-methylbutyl, 1-ethylpropyl, 1,1-dimethylpropyl, 1,2-dimethylpropyl, 2-methylbutyl, 3-methylbutyl, 2,2-dimethylpropyl, 1-methylpentyl, 1-ethylbutyl, 2-ethylbutyl, 1-ethyl-1-methylpropyl, 1-ethyl-2-methylpropyl, 1,1-dimethylbutyl, 1,2-dimethylbutyl, 1,3-dimethylbutyl, 2-methylpentyl, 3-methylpentyl, 4-methylpentyl, 2,3-dimethylbutyl, 1-methylhexyl, 1-ethylpentyl, 2-ethylpentyl, 1-propylbutyl, 2-methyl-3-hexyl, 1,2-dimethylpentyl, 1,3-dimethylpentyl, 1,4-dimethylpentyl, 1-ethyl-1-methylbutyl, 1-methyl-2-ethylbutyl, 1-ethyl-2-methylbutyl, 1-ethyl-3-methylbutyl, 1,1-dimethylpentyl, 1,1,3-trimethylbutyl, 1,1-diethylpropyl, 2-methylhexyl, 3-methylhexyl, 4-methylhexyl, 5-methylhexyl, 3-ethylpentyl, 1-methylheptyl, 2-methylheptyl, 3-methylheptyl, 4-methylheptyl, 5-methylheptyl, 6-methylheptyl, 1-ethylhexyl, 2-ethylhexyl, 3-ethylhexyl, 1-propylpentyl, 2-propylpentyl, 1,5-dimethylhexyl, 1-ethyl-4-methylpentyl, 1-propyl-3-methylbutyl, 1,1-dimethylhexyl, 1-ethyl-1-methylpentyl and 1,1-diethylbutyl groups.

In the present invention, a C1-4 alkyl group includes a linear or branched C1-4 alkyl group. Examples of the C1-4 alkyl group include methyl, ethyl, propyl, butyl, isopropyl, isobutyl, sec-butyl and tert-butyl groups.

In the present invention, a C1-2 alkyl group includes methyl and ethyl groups.

In the present invention, a C1-4 haloalkyl group includes a fluoromethyl group, a chloromethyl group, a bromomethyl group, a iodomethyl group, a difluoromethyl group, a trifluoromethyl group, a 1-fluoroethyl group, a 2-fluoroethyl group, a 2-chloroethyl group, a pentafluoroethyl group, a 1-fluoropropyl group, a 2-chloropropyl group, a 3-fluoropropyl group, a 3-chloropropyl group, a 4,4,4-trifluorobutyl group and a 4-bromobutyl group.

In the present invention, a C1-4 alkoxy group includes methoxy, ethoxy, propoxy, isopropoxy, butoxy, isobutoxy, sec-butoxy and tert-butoxy groups.

In the present invention, a C1-4 haloalkoxy group includes a trifluoromethoxy group, a trichloromethoxy group, a chloromethoxy group, a bromomethoxy group, a fluoromethoxy group, a iodomethoxy group, a difluoromethoxy group, a dibromomethoxy group, a 2-chloroethoxy group, a 2,2,2-trifluoroethoxy group, a 2,2,2-trichloroethoxy group, a 3-bromopropoxy group, a 3-chloropropoxy group, a 2,3-dichloropropoxy group, a 1-fluorobutoxy group, a 4-fluorobutoxy group and a 1-chlorobutoxy group.

In the present invention, examples of a C1-12 alkylene group includes methylene, ethylene, propylene, butylene, pentylene, hexylene, heptylene, octylene, nonylene, decylene, undecylene and dodecylene groups.
In the present invention, examples of a C1-6 alkylene group means methylene, ethylene, propylene, butylene, pentylene and hexylene groups.

In the present invention, examples of a C2-12 alkenylene group includes ethenylene, propenylene, butenylene, pentenylene, hexenylene, heptenylene, octenylene, nonenylene, decenylene, undecenylene, dodecenylene, butadienylene, pentadienylene, hexadienylene, heptadienylene, octadienylene, nonadienylene, decadienylene, undecadienylene and dodecadienylene groups.

In the present invention, examples of a C2-6 alkenylene group includes ethenylene, propenylene, butenylene, pentenylene, hexenylene, butadienylene, pentadienylene and hexadienylene groups.

In the present invention, examples of a C2-12 alkynylene group includes ethynylene, propynylene, butynylene, pentynylene, hexynylene, heptynylene, octynylene, nonynylene, decynylene, undecynylene, dodecynylene, butadiynylene, pentadiynylene, hexadiynylene, heptadiynylene, octadiynylene, nonadiynylene, decadiynylene, undecadiynylene and dodecadiynylene groups.

In the present invention, examples of a C2-6 alkynylene group includes ethynylene, propynylene, butynylene, pentynylene, hexynylene, butadiynylene, pentadiynylene and hexadiynylene groups.

In the present invention, examples of an acidic group includes a carboxyl group, a hydroxy group, a hydroxamic acid group, a sulfonic acid group, a boronic acid group, a carbamoyl group, a sulfamoyl group, a sulfoximine group (—SH(=O)(=NH)) and a tetrazolyl group.

In the present invention, a C3-10 carbocyclic ring refers to a carbocyclic ring which is a C3-10 monocyclic or bicyclic carbocyclic ring and which may be partially or wholly saturated. Examples of the C3-10 carbocyclic ring include cyclopropane, cyclobutane, cyclopentane, cyclohexane, cycloheptane, cyclooctane, cyclononane, cyclodecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene and perhydronaphthalene.

In the present invention, a C3-10 carbocyclic ring include a bridged carbobicyclic ring. Examples of a C3-10 bridged carbobicyclic ring include bicyclo[4.2.0]octa-1,3,5-triene, bicyclo[2.2.1]heptane, bicyclo[2.2.1]hepta-2-ene, bicyclo[3.1.1]heptane, bicyclo[3.1.1]hepta-2-ene, bicyclo[3.2.1]octane, bicyclo[2.2.2]octane, bicyclo[2.2.2]octa-2-ene, adamantine, noradamantine and cubane ring.

In the present invention, a 3- to 10-membered heterocyclic ring refers to a partially or wholly saturated 3- to 10-membered monocyclic or bicyclic heterocyclic ring which contains 1 to 5 heteroatoms selected from an oxygen atom, a nitrogen atom and a sulfur atom. Examples of the 3- to 10-membered heterocyclic ring include pyrrole, imidazole, triazole, tetrazole, pyrazole, pyridine, pyrazine, pyrimidine, pyridazine, azepine, diazepine, furan, pyran, oxepin, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzofurazan, benzothiadiazole, benzotriazole, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepin, tetrahydrooxepin, perhydrooxepin, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dioxolane, dioxane, dithiolane, dithiane, dioxaindane, benzodioxane, chromane, benzodithiolane and benzodithiane rings.

In the present invention, a C3-7 carbocyclic ring means a C3-7 monocyclic carbocyclic ring which may be partially or wholly saturated, for example, the C3-7 carbocyclic ring include cyclopropane, cyclobutane, cyclopentane, cyclohexane, cycloheptane, cyclopentene, cyclohexene, cycloheptene, cyclobutadiene, cyclopentadiene, cyclohexadiene, cycloheptadiene and benzene rings.

In the present invention, a C3-7 saturated carbocyclic ring include cyclopropane, cyclobutane, cyclopentane, cyclohexane and cycloheptane rings.

In the present invention, a C3-4 saturated carbocyclic ring include cyclopropane and cyclobutane rings.

In the present invention, a 3- to 7-membered heterocyclic ring includes a 3- to 7-membered unsaturated heterocyclic ring and a 3- to 7-membered saturated heterocyclic ring. Examples of the 3- to 7-membered heterocyclic ring include aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepin, tetrahydrooxepin, perhydrooxepin, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, dioxolane, dioxane, dithiolane, dithiane, pyrrole, imidazole, triazole, tetrazole, pyrazole, pyridine, pyrazine, pyrimidine, pyridazine, azepine, diazepine, furan, pyran, oxepin, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine and thiadiazepine rings.

In the present invention, examples of the 3- to 7-membered saturated heterocyclic ring include aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepin, tetrahydrooxepin, perhydrooxepin, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, dioxolane, dioxane, dithiolane, dithiane rings.

In the present invention, the 3- to 7-membered nitrogen-containing saturated heterocyclic ring means the 3- to 7-membered saturated heterocyclic ring which contains at least 1 nitrogen atom. Examples of the 3- to 7-membered nitrogen-containing saturated heterocyclic ring include aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine rings.

In the present invention, Y is preferably —$CH_2$—, or —O—.

In the present invention, a bond direction of $W^4$ or W is not particularly limited.

In the present invention, $R^1$ is preferably a -L-ring3-.

In the present invention, a bond direction of $R^1$ is not particularly limited.

In the present invention, ring1 is preferably a C3-10 carbocyclic ring and cyclobutane, cyclohexane, benzene, bicyclo[4.2.0]octa-1,3,5-triene, indane, naphthalene or tetrahydronaphthalene ring is even more preferable.

In the present invention, ring1 is also preferably a 3- to 7-membered heterocyclic ring and thiazole, isothiazole, pyridine, pyrrolidine, tetrahydropyran or pyrazole ring is even more preferable.

In the present invention, ring2 is preferably a C3-7 carbocyclic ring and a cyclopropane ring is even more preferable.

In the present invention, ring3 is preferably a C3-7 saturated carbocyclic ring which may be substituted with a C1-4 alkyl group, and cyclopropane, cyclobutane or cyclopentane ring is even more preferable.

In the present invention, ring3 is also preferably a 3- to 7-membered saturated heterocyclic ring which may be substituted with a C1-4 alkyl group, and azetidine or pyrrolidine ring is even more preferable.

In the present invention, compounds described in Examples are more preferable. In the present invention, 4-[6-(3-Phenylpropoxy)-1,2,4,5-tetrahydro-3H-3-benzazepin-3-yl]butanoic acid, 4-{6-[2-(1-Naphthyl)ethoxy]-1,2,4,5-tetrahydro-3H-3-benzazepin-3-yl}butanoic acid or 1-{8-[2-(1-Naphthyl)ethoxy]-1,2,3,4-tetrahydro-2-naphthalenyl}-3-azetidinecarboxylic acid is more preferable.

[Isomers]

Unless otherwise specifically indicated, all isomers are included in the present invention. For example, an alkyl group includes linear and branched ones. In addition, all of geometric isomers due to double bond(s), ring(s) and fused ring(s) ((E)-, (Z)-, cis- and trans-forms), optical isomers due to the presence of asymmetric carbon atom(s) and the like (R-, S-, α- and, β-configurations, enantiomer(s) and diastereomer(s)), optically active substances having optical rotation (D-, L-, d- and l-forms), polar substances by chromatographic separation (more polar and less polar substances), compounds in equilibrium, rotational isomers, a mixture thereof in any proportion and a racemic mixture are included in the present invention. In addition, tautomers are all included in the present invention.

Further, optical isomers in the present invention may include, not only 100%-pure isomers, but also less than 50%-pure optical isomers.

In the present invention, unless otherwise specified, the symbol: 
represents that a substituent binds to the back side on the paper surface (in other words, α-configuration), the symbol: 
represents that a substituent binds to the front side on the paper surface (in other words, β-configuration), and the symbol: 
represents α-configuration, β-configuration or a mixture thereof at an appropriate ratio, as would be apparent to those skilled in the art.

The compound represented by general formula (I-1) can be converted into a corresponding pharmaceutically acceptable salt by a known method. The pharmaceutically acceptable salt is preferably a water-soluble salt. Examples of the appropriate salt include a salt of an alkali metal (such as potassium and sodium), a salt of an alkaline earth metal (such as calcium and magnesium), an ammonium salt, a salt of a pharmaceutically acceptable organic amine (such as tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine and N-methyl-D-glucamine) as well as an acid addition salt (such as a salt of an inorganic acid (such as a hydrochloride, a hydrobromide, a hydroiodide, a sulfate, a phosphate and a nitrate) and a salt of an organic acid (such as an acetate, a trifluoroacetate, a lactate, a tartrate, an oxalate, a fumarate, a maleate, a benzoate, a citrate, a methanesulfonate, an ethanesulfonate, a benzenesulfonate, a toluenesulfonate, an isethionate, a glucuronate and a gluconate)) and the like.

The compound represented by general formula (I-1) or a pharmaceutically acceptable salt thereof can be also converted into a solvate. The solvate is preferably a low-toxicity and water-soluble solvate. Examples of the appropriate solvate include a solvate of water and a solvate of an alcohol based solvent (such as a solvate of ethanol).

The compound represented by general formula (I-1) can be converted into a corresponding N-oxide by a known method. An N-oxide of the compound represented by general formula (I-1) represents a compound obtained by oxidation a nitrogen atom in the compound represented by general formula (I-1). In addition, the N-oxide of the compound represented by general formula (I) may be further converted to the above-described alkali (alkaline earth) metal salt, the ammonium salt, the organic amine salt or the acid addition salt.

The compound represented by the general formula (I-1) can form a cocrystal with an appropriate cocrystal former. As the cocrystal, pharmaceutically acceptable cocrystal that is formed with a pharmaceutically acceptable cocrystal former is preferable. The cocrystal is defined as a crystal that is formed of two or more different molecules by intermolecular interaction that is different from ionic bond. Furthermore, the cocrystal may be a composite of a neutral molecule and a salt. The cocrystal can be prepared by a well-known method, for example, melting crystallization, recrystallization from a solvent, or physically pulverizing the components together. Appropriate cocrystal formers include ones described in WO2006/007448, for example, 4-aminobenzoic acid, 4-aminopyridine, adenine, alanine, acetyl salicylic acid and the like can be mentioned.

In addition, the compound represented by general formula (I-1) may be dosed as a prodrug. The prodrug of the compound represented by general formula (I-1) refers to a compound which is converted to the compound represented by general formula (I-1) by a reaction with an enzyme, gastric acid and the like in vivo. Examples of the prodrug of the compound represented by general formula (I-1) include the followings: when the compound represented by general formula (I-1) has a hydroxy group, a compound obtained by making the hydroxy group in the compound represented by general formula (I-1) is acylated, alkylated, phosphorylated or borated (for example, a compound obtained by making the hydroxy group in the compound of the present invention is acetylated, palmitoylated, propanoylated, pivaloylated, succinylated, fumarylated, alanylated, dimethylaminomethylcarbonylated or the like); a compound obtained by making a carboxyl group in the compound represented by general formula (I-1) is esterified or amidated (for example, a compound obtained by making a carboxyl group in the compound represented by general formula (I-1) is an ethyl ester, an isopropyl ester, a phenyl ester, a carboxymethyl ester, a dimethylaminomethyl ester, a pivaloyloxymethyl ester, an ethoxycarbonyloxyethyl ester, a phthalidyl ester, a (5-methyl-2-oxo-1,3-dioxolen-4-yl)methyl ester, a cyclohexyloxycarbonylethyl ester, a methylamide or the like); and the like. These compounds can be prepared by a known method. In addition, the prodrug of the compound represented by general formula (I-1) may be either a hydrate or a non-hydrate. Further, the prodrug of the compound represented by general formula (I-1) may be a compound which is converted to the compound represented by general formula (I-1) under a physiological condition as described in "*Iyakuhin no kaihatsu*", Vol. 7, "*Bunshi sekkei*", pages 163-198, Hirokawa-Shoten Ltd., published 1990.

Furthermore, the compound represented by general formula (I-1) may also be labeled by an isotope (for example, $^2$H, $^3$H, $^{11}$C, $^{13}$C, $^{14}$C, $^{13}$N, $^{15}$N, $^{15}$O, $^{17}$O, $^{18}$O, $^{35}$S, $^{18}$F, $^{36}$Cl, $^{123}$I, $^{125}$I and the like) and the like.

[Processes for the Preparation of the Compound of the Present Invention]

The compound of the present invention can be prepared by a known method. For example, the compound of the present invention can be prepared by appropriately improving a method described in Comprehensive Organic Transformations: A Guide to Functional Group Preparations, 2nd Edition (Richard C. Larock, John Wiley & Sons Inc., 1999) or the methods described in Examples and the like or combining these methods.

In general formula (I), a compound in which $X^1$ and $X^2$ is either $CH_2$, $R^1$ is -L-ring3-, L is a bond, Y is —O— and ring3 is a 3- to 7-membered nitrogen-containing saturated heterocyclic ring, i.e., a compound represented by general formula (I-A):

[Chemical Formula 12]

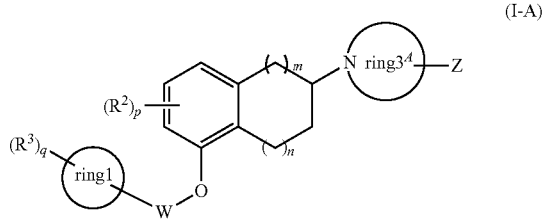

(I-A)

(wherein, ring$3^A$ represents a 3- to 7-membered nitrogen-containing saturated heterocyclic ring and all the symbols represent the same meanings as described above) can be prepared by Reaction Scheme 1 shown below.

Reaction Scheme 1

[Chemical Formula 13]

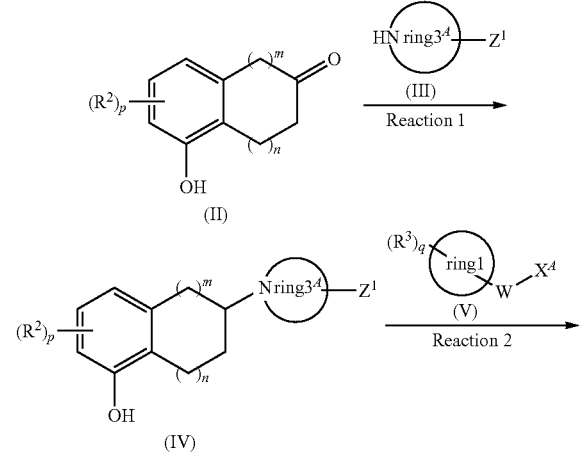

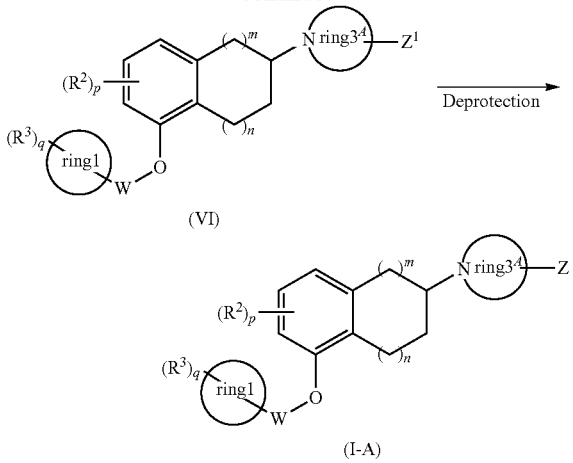

(wherein, $X^A$ represents a halogen atom or a hydroxyl group, $Z^1$ represents an acidic group which may be protected, and other symbols have the same meanings as described above).

In Reaction Scheme 1, Reaction 1 can be performed by subjecting a compound represented by general formula (II) and a compound represented by general formula (III) to a reductive amination reaction. The reductive amination reaction is known, and for example, is performed in an organic solvent (such as dichloroethane, dichloromethane, tetrahydrofuran, toluene and N,N-dimethylformamide) using a compound represented by general formula (III) in the presence of a reducing agent (such as sodium triacetoxyborohydride, sodium cyanoborohydride and pinacolborane) at a temperature of 0 to 70° C.

In Reaction Scheme 1, Reaction 2 can be performed by subjecting a compound represented by general formula (IV) and a compound represented by general formula (V) to an etherification reaction. The etherification reaction is known, and can be carried out by (1) substituent reaction when $X^A$ is a halogen atom, and (2) mitsunobu reaction when $X^A$ is a hydroxy group.

(1) Substituent reaction, for example, is performed by a reaction in an organic solvent (such as N,N-dimethylformamide, N,N-dimethylacetamide, dimethyl sulfoxide, chloroform, dichloromethane, diethyl ether, tetrahydrofuran and methyl t-butyl ether) in the presence of a hydroxide of an alkali metal (such as sodium hydroxide, potassium hydroxide and lithium hydroxide), a hydroxide of an alkaline earth metal (such as barium hydroxide and calcium hydroxide), a carbonate (such as sodium carbonate and potassium carbonate), an aqueous solution thereof or a mixture thereof at 0 to 100° C.

(2) Mitsunobu reaction, for example, is performed by a reaction in an organic solvent (such as dichloromethane, diethyl ether, tetrahydrofuran, acetonitrile, benzene and toluene) in the presence of an azo compound (such as diethyl azodicarboxylate (DEAD), diisopropyl azodicarboxylate, 1,1'-(azodicarbonyl)dipiperidine (ADDP), 1,1'-azobis(N,N-dimethylformamide)) and phosphine compound (such as triphenylphosphine, tributylphosphine, trimethylphosphine, polymer-bounded triphenylphosphine) at 0 to 100° C.

In Reaction Scheme 1, a compound represented by general formula (I-A) can be produced by subjecting a compound represented by general formula (VI) prepared in Reaction 2 to a deprotection reaction.

The deprotection reaction is known, and for example, is performed by a method shown below (1) a deprotection reaction by alkaline hydrolysis, (2) a deprotection reaction under an acidic condition, (3) a deprotection reaction by hydrogenolysis, (4) a deprotection reaction of a silyl group, (5) a deprotection reaction by using a metal, (6) a deprotection reaction by using a metal complex and the like.

These methods are described specifically as follows.

(1) A deprotection reaction by alkaline hydrolysis is performed, for example, in an organic solvent (such as methanol, tetrahydrofuran and dioxane), by using a hydroxide of an alkali metal (such as sodium hydroxide, potassium hydroxide and lithium hydroxide), a hydroxide of an alkaline earth metal (such as barium hydroxide and calcium hydroxide), a carbonate (such as sodium carbonate and potassium carbonate), an aqueous solution thereof or a mixture thereof at 0 to 40° C.

(2) A deprotection reaction under an acidic condition is performed, for example, in an organic solvent (such as dichloromethane, chloroform, dioxane, ethyl acetate, methanol, isopropyl alcohol, tetrahydrofuran and anisole), in an organic acid (such as acetic acid, trifluoroacetic acid, methanesulfonic acid and p-tosylic acid), an inorganic acid (such as hydrochloric acid and sulfuric acid) or a mixture thereof (such as hydrobromic acid/acetic acid) in the presence or absence of 2,2,2-trifluoroethanol at 0 to 100° C.

(3) A deprotection reaction by hydrogenolysis is performed, for example, in a solvent (such as an ether-based solvent (such as tetrahydrofuran, dioxane, dimethoxyethane and diethyl ether), an alcohol-based solvent (such as methanol and ethanol), a benzene-based solvent (such as benzene and toluene), a ketone-based solvent (such as acetone and methyl ethyl ketone), a nitrile-based solvent (such as acetonitrile), an amide-based solvent (such as N,N-dimethylformamide), water, ethyl acetate, acetic acid or a mixed solvent of two or more of them), in the presence of a catalyst (such as a palladium-carbon, a palladium black, a palladium hydroxide-carbon, a platinum oxide and a Raney nickel), under hydrogen atmosphere at a normal pressure or under pressurization or in the presence of ammonium formate, at 0 to 200° C.

(4) A deprotection reaction of a silyl group is performed, for example, in a water-miscible organic solvent (such as tetrahydrofuran and acetonitrile), by using tetrabutylammonium fluoride at 0 to 40° C. In addition, a deprotection reaction of a silyl group is performed, for example, in an organic acid (such as acetic acid, trifluoroacetic acid, methanesulfonic acid and p-tosylic acid), an inorganic acid (such as hydrochloric acid and sulfuric acid) or a mixture thereof (such as hydrobromic acid/acetic acid) at −10 to 100° C.

(5) A deprotection reaction by using a metal is performed, for example, in an acidic solvent (such as acetic acid, a buffer solution of pH 4.2 to 7.2 or a mixed solution of such a solution and an organic solvent such as tetrahydrofuran), in the presence of powdery zinc, if necessary, while applying an ultrasonic wave, at 0 to 40° C.

(6) A deprotection reaction by using a metal complex is performed, for example, in an organic solvent (such as dichloromethane, N,N-dimethylformamide, tetrahydrofuran, ethyl acetate, acetonitrile, dioxane and ethanol), water or a mixed solvent thereof, in the presence of a trapping reagent (such as tributyltin hydride, triethylsilane, dimedone, morpholine, diethylamine and pyrrolidine), an organic acid (such as acetic acid, formic acid and 2-ethylhexanoic acid) and/or a salt of an organic acid (such as sodium 2-ethylhexanoate and potassium 2-ethylhexanoate), in the presence or absence of a phosphine-based reagent (such as triphenylphosphine), by using a metal complex (such as tetrakis(triphenylphosphine)palladium (0), bis(triphenylphosphine)palladium (II) dichloride, palladium (II) acetate and chlorotris(triphenylphosphine)rhodium (I)), at 0 to 40° C.

In addition to the above-described methods, a deprotection reaction can be performed, for example, by a method described in T. W. Greene, Protective Groups in Organic Synthesis, Wiley, New York, 1999.

Examples of the protecting group of a hydroxy group include a methyl group, a trityl group, a methoxymethyl (MOM) group, a 1-ethoxyethyl (EE) group, a methoxyethoxymethyl (MEM) group, a 2-tetrahydropyranyl (THP) group, a trimethylsilyl (TMS) group, a triethylsilyl (TES) group, a t-butyldimethylsilyl (TBDMS) group, a t-butyldiphenylsilyl (TBDPS) group, an acetyl (Ac) group, a pivaloyl group, a benzoyl group, a benzyl (Bn) group, a p-methoxybenzyl group, an allyloxycarbonyl (Alloc) group, a 2,2,2-trichloroethoxycarbonyl (Troc) group and the like.

The protecting groups of a hydroxy group are not particularly limited to those described above as long as the protecting groups can be eliminated easily and selectively. For example, the protecting groups described in T. W. Greene, Protective Groups in Organic Synthesis, Wiley, New York, 1999 are used.

In general formula (I-1), a compound in which both $X^1$ and $X^2$ is $CH_2$, $R^1$ is -L-ring3-, L is a bond, Y is —O— and ring3 is a 3- to 7-membered nitrogen-containing saturated heterocyclic ring, i.e., a compound represented by general formula (I-A)':

[Chemical Formula 14]

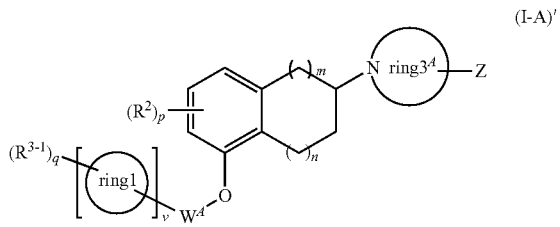

(I-A)'

(wherein, all the symbols represent the same meanings as described above) can be prepared by Reaction Scheme 1-1 shown below.

Reaction Scheme 1-1

[Chemical Formula 15]

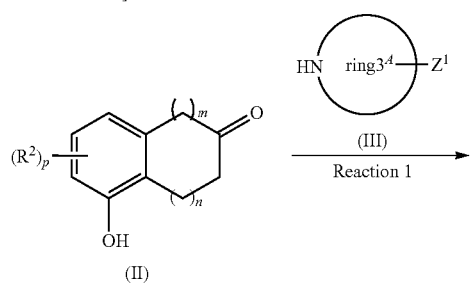

-continued

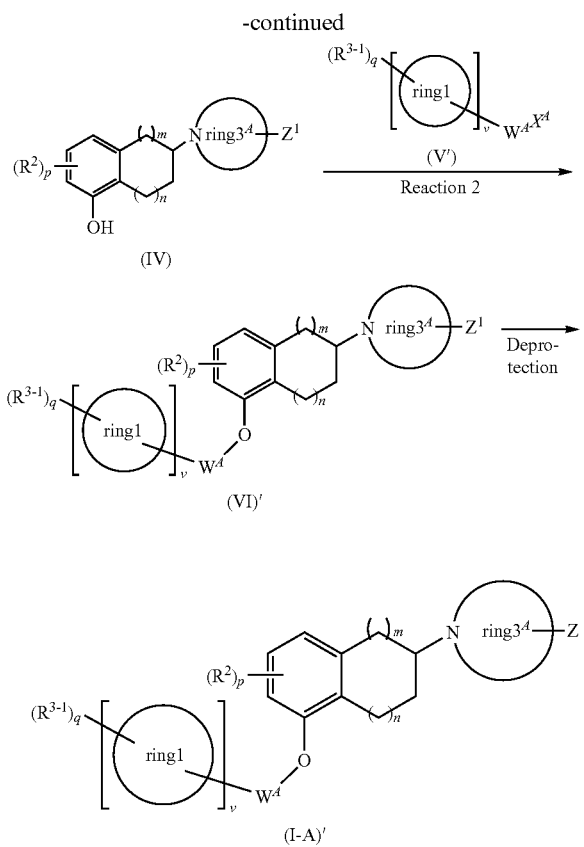

(wherein, all the symbols represent the same meanings as described above)

In Reaction Scheme 1-1, a compound represented by general formula (VI)' can be prepared by the same method according to the above Reaction 2 using a compound represented by general formula (IV) and a compound represented by general formula (V)'.

In Reaction Scheme 1-1, a compound represented by general formula (I-A)' can be prepared by subjecting a compound represented by general formula (VI)' to an above mentioned deprotection reaction.

In general formula (I), in which any one of the $X^1$ or $X^2$ is N, $R^1$ is -L- or -L-ring3-, Y is —O— and ring3 is a C3-7 carbocyclic ring, i.e., a compound represented by general formula (I-B)

[Chemical Formula 16]

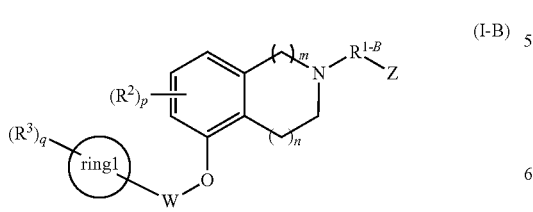

(wherein, $R^{1-B}$ represents -L- or -L-ring3$^B$-, ring3$^B$ represents a C3-7 carbocyclic ring and other symbols represent the same meanings as described above) can be prepared by Reaction Scheme 2 shown below.

Reaction Scheme 2

[Chemical Formula 17]

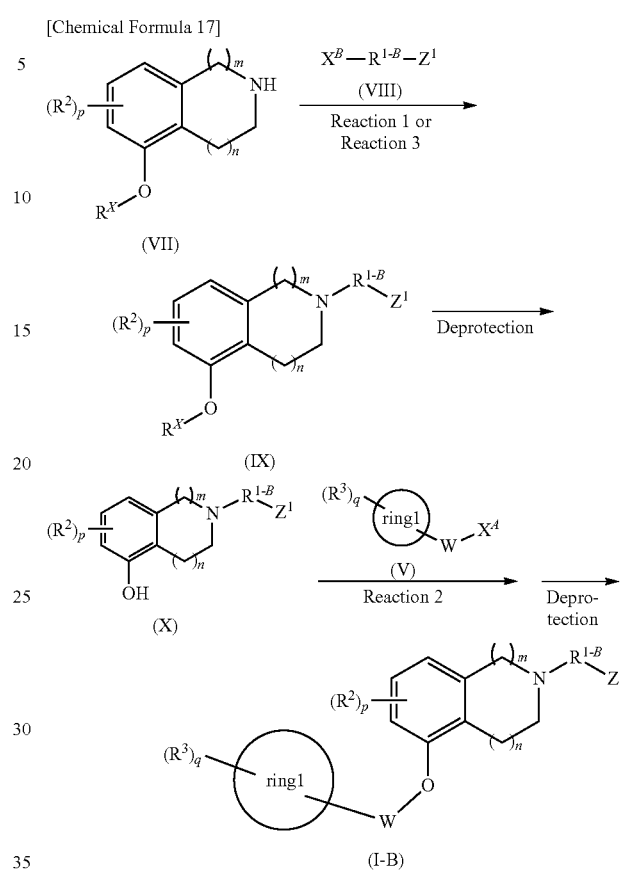

(wherein, $R^X$ represents a protecting group of a hydroxy group, $X^B$ represents a halogen atom or an oxo group and other symbols represent the same meanings as described above)

In a compound represented by general formula (VIII), when $R^{1-B}$ represents -L-, a compound represented by general formula (IX) can be prepared by subjecting a compound represented by general formula (VII) and a compound represented by general formula (VIII) to Reaction 3. Reaction 3 is known, and for example, is performed in an organic solvent (such as N,N-dimethylformamide, dimethylacetamide, dimethyl sulfoxide, chloroform, diethyl ether, tetrahydrofuran and methyl t-butyl ether), in the presence of base (such as potassium carbonate and sodium carbonate), at 0 to 100° C.

In a compound represented by general formula (VIII), when $R^{1-B}$ represents -L-ring3$^B$-, a compound represented by general formula (IX) can be prepared by subjecting a compound represented by general formula (VII) and a compound represented by general formula (VIII) to an above mentioned Reaction 1.

A compound represented by general formula (X) can be prepared by subjecting a compound represented by general formula (IX) to an above mentioned deprotection reaction.

A compound represented by general formula (I-B) can be prepared by subjecting the compound represented by general formula (X) and the compound represented by the general formula (V) to the above mentioned Reaction 2 and, if necessary, subjecting to deprotection reaction.

In general formula (I-1), in which any one of the $X^1$ or $X^2$ is N, $R^1$ is -L- or -L-ring3-, Y is —O— and ring3 is a C3-7 carbocyclic ring, i.e., a compound represented by general formula (I-B)′

[Chemical Formula 18]

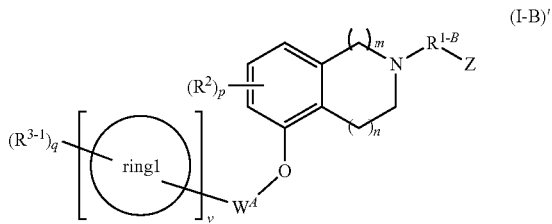

(I-B)′

(wherein, all the symbols represent the same meanings as described above) can be prepared by Reaction Scheme 2-1 shown below.

Reaction Scheme 2-1

[Chemical Formula 19]

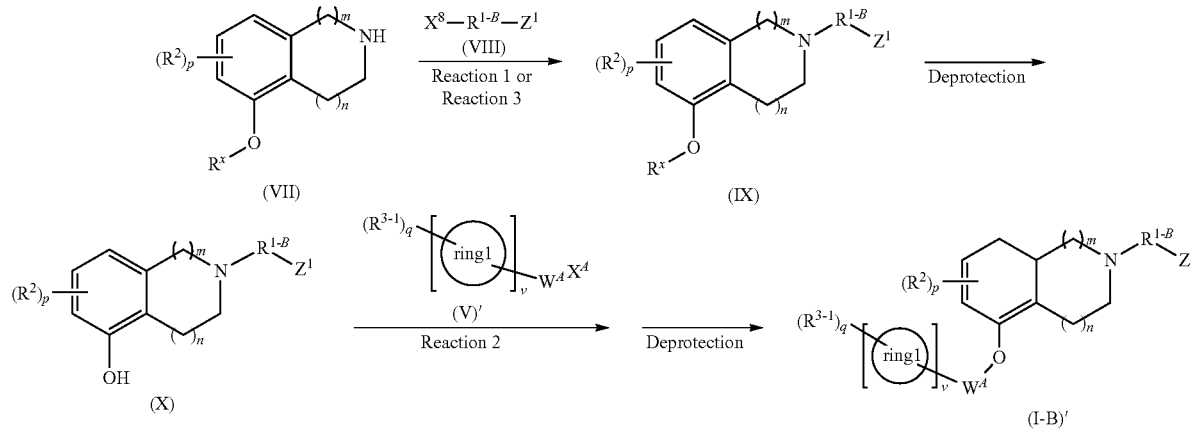

(wherein, all the symbols represent the same meanings as described above)

A compound represented by general formula (I-B)′ can be prepared by subjecting the compound represented by general formula (X) and the compound represented by general formula (V)′ to the above mentioned Reaction 2 and, if necessary, subjecting to deprotection reaction.

In the present specification, the compound used as the starting material in each of the reactions, for example, the compound represented by general formula (II), (III), (V), (V)′, (VII) or (VIII) is known or can be easily prepared by a known method.

In the present specification, a reaction which involves heating in each of the reactions can be performed by using a water bath, an oil bath, a sand bath or a microwave as apparent to those skilled in the art.

In the present specification, a solid phase-supported reagent which is supported by a macromolecular polymer (such as polystyrene, polyacrylamide, polypropylene and polyethylene glycol) may reactions.

In the present specification, the reaction product in each of the reactions can be purified by a conventional purification means. Examples of the purification means include distillation under a normal pressure or reduced pressure, high performance liquid chromatography which uses silica gel or magnesium silicate, thin-layer chromatography, an ion exchange resin, a scavenger resin, column chromatography, washing, recrystallization and the like. The purification may be performed at each of reactions or may be performed after the completion of several reactions.

[Toxicity]

The toxicity of the compound of the present invention is sufficiently low, and the compound of the present invention can be used as a pharmaceutical safely.

[Application to Pharmaceuticals]

The compound of the present invention has an $S1P_5$ (EDG-8) receptor binding activity and modulate the function of it, and therefore, is useful as an agent for preventing and/or treating $S1P_5$ mediated disease. Examples of the $S1P_5$ mediated disease include neurodegenerative disease, autoimmune disease, infection, cancer and the like.

In addition, the compound of the present invention has an $S1P_5$ (EDG-8) receptor binding activity and modulate the function of it, and therefore, is useful as an agent for preventing and/or treating cancer through the activating action of the tumor immunity.

In the present invention, examples of the neurodegenerative disease include anxiety-related disease (social anxiety disorder, anxiety neurosis, obsessive-compulsive disorder and Post-Traumatic Stress Disorder (PTSD)), polyglutamine disease, retinitis pigmentosa, neurosis, convulsion, panic disorder, sleep disorder, depression, reactive depression, epilepsy, Parkinson's disease, parkinsonian syndrome, Down's syndrome, schizophrenia, autonomic ataxia, Huntington's disease, Alzheimer's disease, affective disorder (including depressive disorder and bipolar disorder), cognitive impairment, migraine, tension-type headache, cluster headache, dissociative disorder, amyotrophic lateral sclerosis, neuromyelitis optica, optic neuritis, acute disseminated encephalomyelitis, allergic encephalomyelitis, Marchiafava-Bignami disease, Binswanger's disease, progressive multifocal leukoencephalopathy, postinfectious encephalitis, central pontine myelinolysis, adrenoleukodystrophy, multiple system atrophy, Krabbe disease, metachromatic leukodystrophy, Alexander's disease, Canavan disease, Cockayne syndrome, Pelizaeus-Merzbacher disease, Hurler's syndrome, Lowe syndrome, spinal cord injury, transverse myelitis, spinocerebellar degeneration, chronic inflammatory demyelinating polyradiculoneuropathy (CIDP), Guillain-Barre syndrome, phenylketonuria, Refsum's disease, Charcot-Marie-Tooth disease, Gaucher's disease, Niemann-Pick disease, multiple sclerosis, fragile X syndrome, autism, insomnia, nervous cough, psychogenic convulsive seizure, psychogenic syncopal attack, writer's cramp, spasmodic torticollis, neuropathy and the like.

In the present invention, examples of the autoimmune disease include inflammatory bowel disease, arthritis, lupus, rheumatism, psoriatic arthritis, osteoarthritis, Still's disease, juvenile arthritis, type 1 diabetes mellitus, myasthenia gravis, Hashimoto's thyroiditis, iodine thyroiditis, Basedow's disease, Sjogren's syndrome, Addison disease, opsoclonus-myoclonus syndrome, ankylosing spondylitis, antiphospholipid syndrome, aplastic anemia, autoimmune hepatitis, celiac disease, Goodpasture's syndrome, idiopathic thrombocytopenic purpura, scleroderma, primary biliary cirrhosis, Reiter's disease, Takayasu's arteritis, temporal arteritis, warm autoimmune hemolytic anemia, Wegener's granulomatosis, psoriasis, alopecia universalis, Behcet's disease, chronic fatigue syndrome, autonomic neuropathy, endometriosis, interstitial cystitis, myotonia, vulvodynia, systemic lupus erythematosus and the like.

In the present invention, examples of the infection include symptoms which are developed by the infection of a normal cell in vivo with a pathogenic microorganism and proliferation of the pathogenic microorganism. Representative examples of the pathogenic microorganism include one or more kinds of a virus, a bacterium, a fungus and the like. The above-described pathogenic microorganism also includes a rickettsia, a chlamydia, a protozoan, a parasite and the like.

In the present invention, examples of the virus which related to infection include human hepatitis virus (such as hepatitis B virus, hepatitis C virus, hepatitis A virus or hepatitis E virus), human retrovirus, human immunodeficiency virus (such as HIV1 or HIV2), human T-cell leukemia virus, human T-lymphotropic virus (such as HTLV1 or HTLV2), herpes simplex virus type 1, herpes simplex virus type 2, Epstein-Barr (EB) virus, cytomegalovirus, varicella-zoster virus, human herpesvirus (such as human herpesvirus 6), poliovirus, measles virus, rubella virus, Japanese encephalitis virus, mumps virus, influenza virus, common cold virus (such as adenovirus, enterovirus or rhinovirus), virus which causes severe acute respiratory syndrome (SARS), Ebola virus, West Nile virus, flavivirus, echovirus, Coxsackie virus, coronavirus, respiratory syncytial virus, rotavirus, norovirus, sapovirus, measles virus, parvovirus, vaccinia virus, HTL virus, dengue virus, papilloma virus, molluscum contagiosum virus, rabies virus, JC virus, arbovirus, encephalitis virus, hantavirus, Ebola virus and the like.

In the present invention, examples of the bacterium which related to infection include *Vibrio cholerae, Salmonella enterica, Escherichia coli, Legionella, Bacillus anthracis, Helicobacter pylori, Listeria monocytogenes, Mycobacterium tuberculosis*, nontuberculous mycobacteria, *Staphylococcus, Streptococcus, Streptococcus pneumoniae, Neisseria meningitidis, Klebsiella pneumoniae, Serratia, Corynebacterium diphtheriae, Brucella, Bartonella henselae, Erysipelothrix rhusiopathiae, Actinomyces, Borrelia burgdorferi, Clostridium perfringens, Shigella dysenteriae, Yersinia pestis, Clostridium tetani, Enterobacter* and the like.

In the present invention, examples of the fungus which related to infection include *Candida, Aspergillus, Cryptococcus, Blastomyces, Coccidioides, Histoplasma, Paracoccidioides, Sporothrix* and the like.

In the present invention, examples of the protozoan which related to infection include *Plasmodium, Toxoplasma gondii* and the like.

In the present invention, examples of the parasite which related to infection include *Entamoeba histolytica, Ascaris lumbricoides, Babesia, Cryptosporidium, Giardia lamblia, Ancylostoma, Enterobius vermicularis, Schistosoma, Cestoda, Trichinella spiralis, Trichuris trichiura*, and the like.

In the present invention, examples of other microorganisms which related to infection include *Mycoplasma, Spirochaeta* and the like.

In the present invention, examples of cancer include cancer associated with cerebral nerve (such as pediatric brain tumors (for example, neuroblastoma, medulloblastoma, astrocytoma (juvenile pilocytic astrocytoma), ependymoma, craniopharyngioma, germ cell tumors, optic nerve glioma, choroid plexus papilloma and pontine glioma), adult brain tumors (for example, adult astrocytoma, adult malignant astrocytoma, adult glioblastoma, adult ependymoma, adult malignant ependymoma, adult malignant oligodendroglioma, adult medulloblastoma, adult meningioma and adult malignant meningioma), glioma (for example, astrocytoma, oligodendroglioma, ependymoma and brain stem glioma), pituitary adenoma, acoustic schwannoma, retinoblastoma and uveal malignant melanoma), respiratory tract cancer (such as pharyngeal cancer (for example, nasopharyngeal cancer, oropharyngeal cancer and hypopharyngeal cancer), laryngeal cancer, nasal sinus cancer, lung cancer (for example, small cell cancer and non-small-cell cancer), thymoma and mesothelioma), gastrointestinal cancer (such as esophageal cancer, gastric cancer, duodenal cancer and large bowel cancer (for example, colon cancer, rectal cancer and anal cancer)), oral cancer (such as gingival cancer, tongue cancer and salivary gland cancer), urinary system cancer (such as penile cancer, renal pelvis•ureter cancer, renal cell cancer, testicular tumor, prostate cancer and bladder cancer), cancers that affect women (such as vulvar cancer, uterine cancer (for example, cervical cancer and endometrial cancer), uterine sarcoma, trophoblastic disease (for example, hydatidiform mole, choriocarcinoma, placental-site trophoblastic tumor and persistent trophoblastic disease), vaginal cancer, breast cancer, breast sarcoma, ovarian cancer and ovarian germ cell tumor), skin cancer (such as melanoma (malignant melanoma) (for example, malignant lentiginous melanoma, superficial spreading melanoma, nodular melanoma, acral lentiginous melanoma and erosive melanoma), mycosis fungoides, squamous cell carcinoma, basal cell carcinoma, premonitory signs of skin cancer•intraepidermal carcinoma (for example, actinic keratosis, Bowen's disease and Paget's disease), lymphomatoid papulosis, cutaneous CD30 positive anaplastic large cell lymphoma, Sezary syndrome and cutaneous B-cell lymphoma), bone and muscle cancer (such as osteosarcoma, soft tissue sarcoma, rhabdomyosarcoma, synovial sarcoma and liposarcoma), thyroid cancer, carcinoid, liver cancer (hepatoma), hepatoblastoma, bile duct cancer, gallbladder cancer, pancreatic cancer, pancreatic endocrine tumors (such as insulinoma, gastrinoma and VIPoma), carcinoma of unknown primary, hereditary tumors•familial tumors (such as hereditary nonpolyposis colorectal cancer, familial adenomatous polyposis, hereditary breast cancer, ovarian cancer syndrome, Li-Fraumeni syndrome, hereditary melanoma, Wilms' tumor, hereditary papillary renal cell carcinoma, von Hippel-Lindau syndrome and multiple endocrine neoplasia), leukemia (such as acute myeloid leukemia, acute lymphoblastic leukemia, myelodysplastic syndrome, chronic myeloid leukemia•chronic myeloproliferative disorder, adult T-cell leukemia-lymphoma, chronic lymphocytic leukemia and small lymphocytic lymphoma), multiple myeloma, primary macroglobulinemia, malignant lymphoma (such as Hodgkin's lymphoma, intermediate- and high-grade lymphomas, Burkitt's lymphoma, lymphoblastic lymphoma, follicular lymphoma, mantle-cell lymphoma, MALT (Mucosa-Associated Lymphoid Tissue) lymphoma and NK (natural killer) cell lymphoma) and the like.

The compound of the present invention may be administered as a combined medicine by being combined with other drug(s) for the purpose of:
1) complementation and/or enhancement of the preventing and/or treating effect of the compound,
2) improvement in kinetics•absorption, and reduction of the dose of the compound, and/or
3) reduction of the side effect of the compound.

The combined medicine of the compound of the present invention with other drug(s) may be administered in the form of a compounding agent in which both ingredients are compounded in a preparation or may be administered by means of separate preparations. The case of being administered by means of separate preparations includes simultaneous administration and administrations with a time difference. In addition, in the case of the administrations with a time difference, the compound of the present invention may be firstly administered, followed by administration of the other drug(s). Alternatively, the other drug(s) may be firstly administered, followed by administration of the compound of the present invention. A method for administering the compound of the present invention and that for administering the other drug(s) may be the same or different.

The disease which exhibits preventing and/or treating effect by the above-mentioned combined medicine is not particularly limited. The disease may be any disease in which the preventing and/or treating effect of the compound of the present invention is complemented and/or enhanced by the other drug(s). In addition, the other drug(s) which is combined with the compound of the present invention includes not only those which have been found up to now but also those which will be found in future.

Examples of the other drug(s) for complementation and/or enhancement of the preventing and/or treating effect of the compound of the present invention on neurodegenerative disease include an acetylcholinesterase inhibitor, a nicotinic receptor modulator, a suppressor of production, secretion, accumulation, agglutination and/or deposition of β amyloid protein (such as a β secretase inhibitor, a γ secretase inhibitor, a drug having β amyloid protein agglutination inhibitory action, a β amyloid vaccine and a catabolic enzyme of β amyloid), an activator of brain function (such as an activator of brain metabolism and a cerebral circulation improving drug), a dopamine receptor agonist (a dopamine receptor stimulant), a dopamine release accelerating drug (a dopamine secretion accelerating drug or a dopamine release accelerating drug), a dopamine uptake inhibitor, a dopamine agonist, a dopamine antagonist, lithium carbonate, a serotonergic agonist, a serotonin antagonist (such as a 5-$HT_{2A}$ antagonist, a 5-$HT_3$ antagonist, a 5-$HT_4$ antagonist and a 5-$HT_7$ antagonist), a monoamine oxidase (MAO) inhibitor, an aromatic L-amino acid decarboxylase inhibitor (DCI), a norepinephrine (noradrenaline) supplement, an anticholinergic drug, a catechol-O-methyltransferase (COMT) inhibitor, a therapeutic drug for amyotrophic lateral sclerosis, a therapeutic drug for hyperlipidemia, an apoptosis inhibitor, a nerve regeneration•differentiation accelerating drug, an antihypertensive drug, a therapeutic drug for diabetes, a therapeutic drug for diabetic complication, an antidepressant (such as a tricyclic antidepressant and a tetracyclic antidepressant), an antianxiety drug, an antiepileptic drug, an anticonvulsant drug, an antispasmodic drug, a nonsteroidal antiinflammatory drug, an anti-cytokine drug (such as a TNF inhibitor and an MAP kinase inhibitor), a steroid, a sex hormone or a derivative thereof (such as progesterone, estradiol and estradiol benzoate), a thyroid hormone, a parathyroid hormone (such as PTH), a calcium channel blocker (a calcium antagonist), a calcium receptor antagonist, an opioid receptor agonist, an N-methyl-D-2-amino-5-D-aspartate (NMDA) receptor antagonist, a VR-1 receptor agonist, a neuromuscular junction blocking drug, a cannabinoid-2 receptor agonist, a GABAA receptor modulator (such as a GABAA receptor agonist), a GABAB receptor modulator, prostaglandins, a cholecystokinin antagonist, a nitric oxide synthase (NOS) inhibitor, a local anesthetic, a neurotrophic factor (such as neurotrophin, TGF-β superfamily, a neurokinin family and a growth factor), a sympathomimetic drug, a parasympathomimetic drug, a sympatholytic drug, a prostaglandin receptor antagonist, a prostaglandin receptor agonist, a carbonic anhydrase inhibitor, a hyperosmotic drug, a vasodilator drug, a metabolic activator, a diuretic drug (such as a thiazide diuretic drug, a loop diuretic drug and a potassium-sparing diuretic drug), a peripheral blood flow improving drug, an immunosuppressive drug, an immunoglobulin, an α-amino-3-hydroxy-5-methyl-4-isoxazolepropionic acid (AMPA)/kainic acid receptor antagonist, an Rho-kinase inhibitor, vitamins (such as vitamin B6 and vitamin B12), a cyclooxygenase (COX)-2 inhibitor, an anti-dizziness drug, a therapeutic drug for anemia, a therapeutic drug for heavy metal poisoning, a muscarinic receptor agonist, an aldose reductase inhibitor, a nerve regeneration accelerating drug, a protein kinase C (PKC) inhibitor, an advanced glycation end product (AGE) inhibitor, a reactive oxygen species scavenger, a muscle relaxant and the like.

Examples of the other drug(s) for complementation and/or enhancement of the preventing and/or treating effect of the compound of the present invention on autoimmune disease include an immunosuppressive drug, a steroid, a disease-modifying antirheumatic drug, an elastase inhibitor, a cannabinoid-2 receptor agonist, a prostaglandin, a prostaglandin synthase inhibitor, a phosphodiesterase inhibitor, a metalloprotease inhibitor, an adhesion molecule inhibitor, an anti-cytokine protein preparation such as an anti-TNF-α preparation, an anti-IL-1 preparation and an anti-IL-6 preparation, a cytokine inhibitor, a nonsteroidal antiinflammatory drug, an anti-CD 20 antibody and the like.

Examples of the other drug(s) for complementation and/or enhancement of the preventing and/or treating effect of the compound of the present invention on infection include an antiviral drug, an antibiotic, an antifungal drug, an antiparasitic drug, an antiprotozoal drug and the like.

Examples of the other drug(s) for complementation and/or enhancement of the preventing and/or treating effect of the compound of the present invention on cancer include an alkylating drug, an antimetabolite, an anticarcinogenic antibiotic, a plant alkaloid drug, a hormonal drug, a platinum compound, an anti-CD 20 antibody and other anticancer agents. Further, for the purpose of complementation and/or enhancement of the preventing and/or treating effect of the compound of the present invention on cancer, for example, radiation therapy, cell therapy (such as chimeric antigen receptor-expressing T cell (CAR-T) therapy, T cell receptor (TCR) therapy and the like) and the like, may be used together.

The compound of the present invention or the combined medicine is administered as a solid agent for internal use or a solution for oral administration (internal use), a sustained-release preparation in oral administration, or injectables, external preparations, inhalants or suppositories for parenteral administration.

The solid preparations for oral administration (internal use) includs, for example, tablets, pills, capsules, powders and granulars. The capsules include hard capsules and soft capsules.

The oral solid preparation as an oral preparation is prepared, for example, by mixing an active ingredient with an excipient (such as lactose, mannitol, glucose, microcrystalline cellulose and starch), a bonding agent (such as hydroxypropyl cellulose, polyvinylpyrrolidone and magnesium aluminometasilicate), a disintegrating agent (such as calcium cellulose glycolate), a lubricant (such as magnesium stearate), a stabilizer, a solubilizing agent (such as glutamic acid and aspartic acid) and the like by a routine procedure. In addition, if necessary, the active ingredient may be coated with a coating agent (such as white soft sugar, gelatin, hydroxypropyl cellulose and hydroxypropyl methylcellulose phthalate) or may be coated with two or more layers. Further, capsules of substances which can be absorbed, such as gelatin, are also included.

The liquid for oral administration (internal use) includes pharmaceutically acceptable solutions, suspensions, emulsions, syrups and elixirs. In such the liquid formulations, one or more active substances are dissolved, suspended or emulsified in diluents (e.g. purified water, ethanol, or mixed liquids of them etc.) which are generally used. Further, this liquid formulation may contain wetting agents, suspending agents, emulsifiers, sweeteners, flavors, fragrances, preservatives or buffers.

And, sustained-release preparations in oral administration are also effective. A gel forming substance used in these sustained-release preparations is a substance which is swollen while containing a solvent, thereby, mutually linking colloidal particles thereof to have a three dimensional network structure, and can form a jelly-like body which has no flowability. The substance is mainly used as binders, thickeners and sustained-release bases from a view point of preparations. For example, gum arabic, agar, polyvinyl pyrrolidone, sodium alginate, alginic acid propylene glycol ester, carboxyvinyl polymer, carboxymethylcellulose, carboxymethylcellulose sodium, guar gum, gelatin, hydroxypropylmethylcellulose, hydroxypropylcellulose, polyvinyl alcohol, methylcellulose or hydroxyethylmethylcellulose can be used.

Injectables for parenteral administration include solutions, suspensions, emulsions and solid injectables which are used by dissolving or suspending in a solvent upon use. Injectables are used by dissolving, suspending or emulsifying one or more active substances in a solvent. As the solvent, for example, distilled water for injection, physiological saline, vegetable oil, alcohols such as propylene glycol, polyethylene glycol, and ethanol and the like, and a combination of them are used. Further, the injectables may contain stabilizers, solubilization aids (e.g. glutamic acid, aspartic acid, Polysorbate 80 (registered trademark) etc.), suspending agents, emulsifiers, soothing agents, buffers or preservatives. These are produced by sterilization or a sterile operation method at a final step. Alternatively, injectables can be also used as aseptic solid agents (e.g. lyophilized products are produced, and dissolved in distilled water for injection or other solvent which has been sterilized or are aseptic, before use thereof).

A dosage form of the external preparations for parenteral administration includes, for example, spraying agents, inhalants, sprays, aerosols, ointments, gels, creams, fomentations, patches, liniments and nose drops. These contain one or more active substances, and prepared by the known method or formulation which is ordinarily used.

Spraying agents, inhalants and Sprays may contain stabilizers such as sodium hydrogen sulfite and buffers imparting isotonicity, for example, isotonics such as sodium chloride, sodium citrate or citric acid, in addition to diluents which are generally used. A method of producing spraying agents is described in detail, for example, in U.S. Pat. Nos. 2,868,691 and 3,095,355.

The inhalants for parenteral administration include aerosols, powders for inhalation or solutions for inhalation, and the solutions for inhalation may be a form which is used by dissolving or suspending in water or other suitable medium upon use.

These inhalants are produced in accordance with the known method.

For example, in the case of a solution for inhalation, it is prepared by appropriately selecting antiseptics (e.g benzalkonium chloride, paraben etc.), colorants, buffering agents (e.g. sodium phosphate, sodium acetate etc.), isotonizing agents (e.g. sodium chloride, concentrated glycerin etc.), thickeners (e.g. carboxyvinyl polymer etc.), absorption enhancers and the like, if necessary.

In the case of a powder for inhalation, it is prepared by appropriately selecting lubricants (e.g. stearic acid and a salt thereof etc.), binders (e.g. starch, dextrin etc.), excipients (e.g. lactose, cellulose etc.), colorants, antiseptics (e.g benzalkonium chloride, paraben etc.) or absorption enhancers, if necessary.

When solutions for inhalation are administered, usually, a sprayer (e.g. atomizer, nebulizer etc.) is used and, when powders for inhalation are administered, usually, an inhalation administration equipment for powdery drugs is used.

Ointments are produced by formulation which is known or ordinarily used. For example, ointments are prepared by kneading or melting one or more active substances into a base. An ointment base is selected from ointment bases which are known or orginarily used. For example, ointment bases selected from higher fatty acid or higher fatty acid ester (e.g. adipic acid, myristic acid, palmitic acid, stearic acid, oleic acid, adipic acid ester, myristic acid ester, palmitic acid ester, stearic acid ester, oleic acid ester etc.), waxes (e.g. beeswax, whale wax, ceresin etc.), surfactants (e.g. polyoxyethylene alkyl ether phosphoric acid ester etc.), higher alcohols (e.g. cetanol, stearyl alcohol, cetostearyl alcohol etc.), silicone oils (e.g. dimethylpolysiloxane etc.), hydrocarbons (e.g. hydrophilic vaseline, white vaseline, purified lanolin, liquid paraffin etc.), glycols (e.g. ethylene glycol, diethylene glycol, propylene glycol, polyethylene glycol, macrogol etc.), vegetable oils (e.g. castor oil, olive oil, sesame oil, turpentine oil etc.), animal oils (e.g. mink oil, yolk oil, squalane, squalene etc.), water, absorption enhancers or rash preventing agents are used alone, or by mixing two or more kinds. Further, ointment bases may contain humectants, preservatives, stabilizers, antioxidants or flavoring agents.

Gel agents are produced by formulation which is known or ordinarily used. For example, gel agents are prepared by melting one or more active substances into a base. A gel base is selected from gel bases which are known or ordinarily used. For example, gel bases selected from lower alcohols (e.g. ethanol, isopropyl alcohol etc.), gelling agents (e.g. carboxymethylcellulose, hydroxyethylcellulose, hydroxypropylcellulose, ethylcellulose etc.), neutralizing agents (e.g. triethanolamine, diisopropanolamine etc.), surfactants (e.g. monostearic acid polyethylene glycol etc.), gums, water, absorption enhancers and rash preventing agents are used alone, or by mixing two or more kinds. Further, gel bases may contain preservatives, antioxidants or flavoring agents.

Creams are prepared by formulation which is known or ordinarily used. For example, creams are prepared by melting or emulsifying one or more active substances into a base. A cream base is selected from cream bases which are known or ordinarily used. For example, cream bases selected from higher fatty acid esters, lower alcohols, hydrocarbons, polyhydric alcohols (e.g. propylene glycol, 1,3-butylene glycol etc.), higher alcohols (e.g. 2-hexyldecanol, cetanol etc.), emulsifiers (e.g. polyoxyethylene alkyl ethers, fatty acid esters etc.), water, absorption enhancers and rash preventing agents are used alone, or by mixing two or more kinds. Further, cream bases may contain preservatives, antioxidants or flavoring agents.

Fomentations are produced by formulation which is known or ordinarily used. For example, fomentations are produced by melting one or more active substances into a base, and spreading a melt as a kneaded product on a support. A base used for fomentation is selected from bases which are known or ordinarily used. For example, bases selected from thickeners (e.g. polyacrylic acid, polyvinyl pyrrolidone, gum arabic, starch, gelatin, methylcellulose etc.), wetting agents (e.g. urea, glycerin, propylene glycol etc.), fillers (e.g. kaolin, zinc oxide, talc, calcium, magnesium etc.), water, solubilization aids, tackiness imparting agents and rash preventing agents are used alone, or by mixing two or more kinds. Further, bases used for fomentations may contain preservatives, antioxidants or flavoring agents.

Patches are produced by formulation which is known or ordinarily used. For example, patches are produced by melting one or more active substances into a base, and spreading a melt on a support. A base for patches is selected from bases for patches which are known or ordinarily used. For example, bases for patches selected from polymer bases, fats, oils, higher fatty acids, tackiness imparting agents and rash preventing agents are used alone, or by mixing two or more kinds. Further, bases for patches may contain preservatives, antioxidants or flavoring agents.

Liniments are produced by formulation which is known or ordinarily used. For example, liniments are prepared by dissolving, suspending or emulsifying one or more active substances in a base selected from water, alcohols (e.g. ethanol, polyethylene glycol etc.), higher fatty acid, glycerin, soaps, emulsifiers and suspending agents alone, or two or more kinds of them. Further, liniments may contain preservatives, antioxidants or flavoring agents.

Other composition for parenteral administration includes suppositories for rectal administration or pessaries for intravaginal administration, which contain one or more active substances, and are formulated by the conventional method.

An entire content of all patent documents and non-patent documents or reference documents which are explicitly cited in the present specification may be cited herein as a part of the present specification.

In order to use the compound of the present invention or the combined medicine of the compound of the present invention with other drug(s) for the above-described purpose, the compound of the present invention or the combined medicine of the compound of the present invention with other drug(s) is normally administered systemically or locally, in the form of an oral preparation or a parenteral preparation. The dose varies depending on the age, the body weight, the symptom, the therapeutic effect, the method for administration, the duration of the treatment and the like. However, normally, the dose per adult is in the range of from 1 ng to 1,000 mg per administration, from one to several oral administrations per day or the dose per adult is in the rage of from 0.1 ng to 10 mg per administration, from one to several parenteral administrations per day. Alternatively, the dose is continuously administrated intravenously for a period of time in the range of 1 to 24 hours per day. Of course, the dose varies depending on various factors as described above, and therefore, there are some cases in which a dose below the above-described dose is sufficient and there are other cases in which administration of a dose which exceeds the above-described range is required.

EXAMPLES

The present invention will be described in details by referring to Examples hereinbelow, but the present invention is not limited to Examples.

Concerning chromatographic separation or TLC, a solvent in parentheses corresponds to an eluting solvent or a developing solvent employed and a ratio is expressed by volume ratio.

LC-MS/ELSD was performed by any of the following conditions:
Condition A: {column: YMC Triart $C_{18}$ (particle size: 1.9× $10^6$ m; column length: 30×2.0 mm I.D.); flow rate: 1.0 mL/min; column temperature: 30° C.; mobile phase (A): 0.1% trifluoroacetic acid aqueous solution; mobile phase (B): 0.1% trifluoroacetic acid-acetonitrile solution; gradient (the ratio of mobile phase (A):mobile phase (B) is described): [0 min] 95:5; [0.1 min] 95:5; [1.2 min] 5:95; [1.4 min] 5:95; [1.41 min] 95:5; [1.5 min] 95:5; Detector: UV (PDA), ELSD, MS} or
Condition B: {column: Waters ACQUITY BEH $C_{18}$ (particle size: 1.7×$10^6$ m; column length: 30×2.1 mm I.D.); flow rate: 1.0 mL/min; column temperature: 40° C.; mobile phase (A): 0.1% formic acid aqueous solution; mobile phase (B): 0.1% formic acid-acetonitrile solution; gradient (the ratio of mobile phase (A):mobile phase (B) is described): [0 min] 95:5; [0.1 min] 95:5; [1.2 min] 5:95; [1.4 min] 5:95; [1.41 min] 95:5; [1.5 min] 95:5; Detector: UV (PDA), ELSD, MS}.

Concerning NMR, a solvent in parentheses corresponds to a solvent used for the measurement.

The compound names used in the present specification were named using Advanced Chemistry Development's ACD/Name (registered trademark) computer program which is generally denominates a compound according to the IUPAC rules or according to the IUPAC nomenclature.

Example 1: Methyl 1-(5-hydroxy-1,2,3,4-tetrahydro-2-naphthalenyl)-3-azetidinecarboxylate Methyl azetidine-3-carboxylate hydrochloride (111 mg) (CAS registry number: 100202-39-9) and sodium triacetoxyborohydride (260 mg) were added to a Methylene chloride solution (5 mL) of 5-hydroxy-3,4-dihydronaphthalen-2(1H)-one (100 mg) (CAS registry number: 35697-10-0), and the mixture was stirred at room temperature for 16 hours. The reaction solution was diluted with water, and extracted with methylene chloride.

The reaction mixture was cooled to room temperature, diluted with water, and extracted with ethyl acetate. The organic layer was washed with saturated saline, and thereafter, was dried with anhydrous sodium sulfate. The solution was filtrated and distilled off to give the title compound (100 mg) having the following physical properties. The obtained compound was used in the next reaction without purification.

MS (M+H): 262.

Example 2: Methyl 1-[5-({(2E)-3-[4-(trifluoromethyl)phenyl]-2-propen-1-yl}oxy)-1,2,3,4-tetrahydro-2-naphthalenyl]-3-azetidinecarboxylate (E)-1-(3-chloropropa-1-en-1-yl)-4-(trifluoromethyl)benzene (111 mg) was added to an N,N-dimethylformamide (DMF) (3 mL) mixture solution containing the compound (110 mg) prepared in Example 1 and potassium carbonate (174 mg), and the mixture was stirred at 70° C. for 3 hours. The reaction mixture was cooled to room temperature, diluted with water, and extracted with ethyl acetate. The organic layer was washed with saturated saline, and thereafter, was dried with anhydrous sodium sulfate. The solution was filtrated and distilled off to give the title compound (100 mg) having the following physical properties. The obtained compound was used in the next reaction without purification.

MS (M+H): 446.

Example 2 (1): Methyl 1-{8-[2-(1-naphthyl)ethoxy]-1,2,3,4-tetrahydro-2-naphthalenyl}-3-azetidinecarboxylate

[Chemical Formula 20]

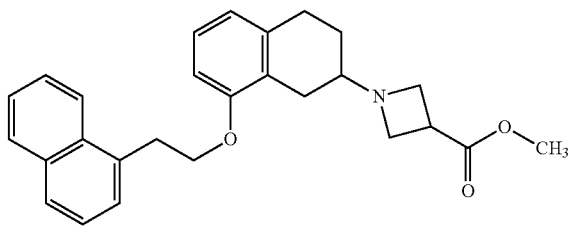

A procedure for a purpose similar to that for Example 2 was carried out by using a corresponding alcohol in place of the compound prepared in Example 1, and a corresponding halide in place of (E)-1-(3-chloropropa-1-en-1-yl)-4-(trifluoromethyl)benzene to give the title compound having the following physical properties.

(LC-MS/ELSD): (Retention time: 0.92 minutes, Condition A);

MS (M+H): 416;

$^1$H-NMR (CDCl$_3$):δ 8.10, 7.86, 7.75, 7.56-7.36, 7.02, 6.67, 6.62, 4.30, 3.74, 3.65-3.52, 3.42-3.24, 2.88-2.61, 2.46-2.34, 2.15, 1.89-1.77, 1.50-1.33.

Example 3: 1-[5-({(2E)-3-[4-(Trifluoromethyl)phenyl]-2-propen-1-yl}oxy)-1,2,3,4-tetrahydro-2-naphthalenyl]-3-azetidinecarboxylic Acid

[Chemical Formula 21]

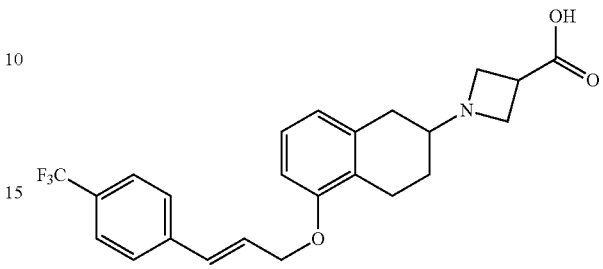

Lithium hydroxide (36 mg) was added to a solution (ethanol (1 mL), tetrahydrofuran (THF) (1 mL) and water (1 mL)) containing the compound (100 mg) prepared in Example 2. The reaction mixture was stirred at room temperature for 16 hours. After that, the solvent was distilled, and the residue liquid was acidified with 2N hydrochloric acid. The resulting solution was purified by reversed phase silica gel column chromatography (water:acetonitrile=10:0→4:6) to give the title compound (60 mg) having the following physical properties.

(LC-MS/ELSD): (Retention time: 0.94 minutes, Condition A);

MS (M+H): 432;

$^1$H-NMR (CD$_3$OD):δ 7.61, 7.14, 6.89-6.81, 6.76, 6.63, 4.75, 4.47-4.38, 3.69-3.62, 3.19, 3.04, 2.80-2.70, 2.27-2.24, 1.77-1.66.

Example 3(1)-3(5)

A procedure for a purpose similar to that for Example 1→Example 2→Example 3 was carried out by using 5-hydroxy-3,4-dihydro-naphthalen-2(1H)-one or a corresponding alcohol, methyl azetidine-3-carboxylate hydrochloride or a corresponding amine, and (E)-1-(3-chloropropa-1-en-1-yl)-4-(trifluoromethyl)benzene or a corresponding halide to give the following Example compounds.

Example 3 (1): 1-[5-({(2E)-3-[4-(Trifluoromethyl)phenyl]-2-propen-1-yl}oxy)-1,2,3,4-tetrahydro-2-naphthalenyl]-3-pyrrolidinecarboxylic Acid (LC-MS/ELSD): (Retention time: 0.94 minutes, Condition A);

MS (M+H): 446.

Example 3 (2): 1-[8-({(2E)-3-[4-(Trifluoromethyl)phenyl]-2-propen-1-yl}oxy)-1,2,3,4-tetrahydro-2-naphthalenyl]-3-azetidinecarboxylic Acid (LC-MS/ELSD): (Retention time: 0.86 minutes, Condition B);

MS (M+H): 432.

Example 3 (3): 3-{Methyl[8-({(2E)-3-[4-(trifluoromethyl)phenyl]-2-propen-1-yl}loxy)-1,2,3,4-tetrahydro-2-naphthalenyl]amino}propanoic Acid (LC-MS/ELSD): (Retention time: 0.86 minutes, Condition B);
MS (M+H): 434.

Example 3 (4): 1-[8-(3-Phenylpropoxy)-1,2,3,4-tetrahydro-2-naphthalenyl]-3-azetidinecarboxylic Acid (LC-MS/ELSD): (Retention time: 0.86 minutes, Condition A);
MS (M+H): 366.

Example 3 (5): 1-{8-[2-(1-Naphthyl)ethoxy]-1,2,3,4-tetrahydro-2-naphthalenyl}-3-azetidinecarboxylic Acid (LC-MS/ELSD): (Retention time: 0.88 minutes, Condition A);
MS (M+H): 402.

Example 4: Ethyl (2E)-3-[4-(trifluoromethyl)phenyl]acrylate

To a suspension of sodium hydride (1.38 g) in THF (40 mL), a solution of triethylphosphonoacetate (7.73 g) in THF (10 mL) was added at 0° C., and the reaction mixture was stirred at room temperature for 30 minutes. To the reaction solution, 4-(Trifluoromethyl)benzaldehyde (CAS registry number: 455-19-6) was added, and the mixture was stirred at room temperature for 1 hour. The reaction mixture was poured into 10% aqueous sodium hydrogen sulfate solution, and extracted with ethyl acetate two times. The organic layer was washed with an aqueous saturated sodium bicarbonate solution and an saturated saline, dried with anhydrous magnesium sulfate, and concentrated under reduced pressure. The obtained residue was purified by silica gel column chromatography (hexane:ethyl acetate=10:0→9:1) to give the title compound (5.92 g) having the following physical properties.
TLC:Rf 0.78 (hexane:ethyl acetate=8:2);
$^1$H-NMR (CDCl$_3$):δ 7.69, 7.64, 6.51, 4.28, 1.35.

Example 5: (2E)-3-[4-(Trifluoromethyl)phenyl]-2-propen-1-ol

To a solution of the compound (5.91 g) prepared in Example 4 in THF (120 mL), 1M toluene solution (50.8 mL) of diisobutylaluminium hydride was added at 0° C., and the mixture was stirred at 0° C. for 30 minutes. The reaction mixture was poured into 2N hydrochloric acid, and extracted with ethyl acetate two times. The organic layer was washed with water, and saturated saline, dried with anhydrous magnesium sulfate, and concentrated under reduced pressure. The obtained residue was purified by silica gel column chromatography (hexane:ethyl acetate=80:20→55:45) to give the title compound (4.46 g) having the following physical properties.
TLC:Rf 0.17 (hexane:ethyl acetate=8:2);
$^1$H-NMR (CDCl$_3$):δ 7.56, 7.47, 6.66, 6.46, 4.37, 1.53.

Example 6: 2-[4-(Trifluoromethyl)phenoxy]ethanol

To a solution of 4-(trifluoromethyl)phenol (500 mg) (CAS registry number: 402-45-9) in DMF (15 mL), potassium carbonate (853 mg) and 2-bromoethanol (771 mg) was added, and the mixture was stirred at 80° C. for 16 hours. The reaction mixture was poured into water, and extracted with ethyl acetate two times. The organic layer was washed with an saturated saline, dried with anhydrous magnesium sulfate, and concentrated under reduced pressure. The obtained residue was purified by silica gel column chromatography (hexane:ethyl acetate=85:15→45:55) to give the title compound (226 mg) having the following physical properties.
$^1$H-NMR (CDCl$_3$):δ 7.55, 6.99, 4.15-4.10, 4.03-3.96, 1.98.

Example 7: (2Z)-3-Phenyl-2-propen-1-ol

To a solution of 3-phenyl-2-propyn-1-ol (800 mg) (CAS registry number: 1504-58-1) and quinoline (780 mg) in ethanol (20 mL), Lindlar's catalyst (160 mg) was added and the mixture was stirred at room temperature for 1 hour under hydrogen atmosphere. The reaction mixture was filtered through Celite (trade name) and the filtrate was concentrated under reduced pressure. The obtained residue was purified by silica gel column chromatography (hexane:ethyl acetate=90:10→60:40) to give the title compound (548 mg) having the following physical properties.
$^1$H-NMR (CDCl$_3$):δ 7.39-7.19, 6.58, 5.89, 4.45, 1.47.

Example 8: rel-[(1R,2S)-2-Phenylcyclopropyl]methanol 1M diethyl zinc solution in hexane (8.9 mL) was diluted with dichloromethane (7.0 mL) and cooled to 0° C. Trifluoroacetic acid (0.689 mL) was added to the solution, and the mixture was stirred at 0° C. for 20 minutes. To the mixture diiodomethane (0.719 mL) was added, and the obtained mixture was stirred at 0° C. for 20 minutes. A solution of the compound (400 mg) prepared in Example 7 in dichloromethane (3 mL) was added to the obtained mixture and the reaction mixture was stirred at 0° C. for 30 minutes, and 3 hours at room temperature. The reaction mixture was poured into 1N hydrochloric acid, and extracted with ethyl acetate two times. The organic layer was washed with saturated saline, dried with anhydrous magnesium sulfate, and concentrated under reduced pressure. The obtained residue was purified by silica gel column chromatography (hexane:ethyl acetate=90:10→60:40) to give the title compound (57.8 mg) having the following physical properties.
$^1$H-NMR (CDCl$_3$):δ 7.36, 7.16, 3.48, 3.27, 2.29, 1.51, 1.05, 0.88.

Example 9: 5-(Benzyloxy)-3,4-dihydro-1(2H)-naphthalenone

Under nitrogen atmosphere, the mixture solution of 5-hydroxy-3,4-dihydronaphthalen-1(2H)-one (10.1 g) (CAS registry number: 28315-93-7), benzylbromide (12.8 g) and potassium carbonate (10.3 g) in DMF (100 mL) was stirred at room temperature for 4 hours. The mixture solution was diluted with ethyl acetate, water was added thereto, and the reaction mixture was extracted with ethyl acetate. The organic layer was sequentially washed with water, 5% aqueous lithium chloride solution and saturated saline, dried with anhydrous sodium sulfate, and concentrated under reduced pressure. The obtained residue was purified by silica gel column chromatography (hexane:ethyl acetate=100:0→60:40) to give the title compound (13.8 g) having the following physical properties.
MS (M+H): 253.

Example 10: 5-(Benzyloxy)-1-methylene-1,2,3,4-tetrahydronaphthalene

To a suspension of the compound (7.83 g) prepared in Example 9 and methyltriphenylphosphoniumiodide (13.8 g) in THF (100 mL), potassium tert-butoxide (46.5 mL, 1M solution in THF) was added dropwise at 0° C. The reaction mixture was stirred at room temperature for 1 hour. To the reaction mixture, cold water was poured, and the mixture was extracted with ethyl acetate. The organic layer was sequentially washed with water and saturated saline, dried with anhydrous sodium sulfate, and concentrated under reduced pressure. The obtained residue was purified by silica gel column chromatography (hexane:ethyl acetate=100:0→80:20) to give the title compound (6.57 g) having the following physical properties.

$^1$H-NMR (CDCl$_3$): δ 7.45-7.25, 7.11, 6.79, 5.46, 5.07, 4.96, 2.84, 2.52-2.48, 1.93-1.87.

Example 11: 1-(Benzyloxy)-5,7,8,9-tetrahydro-6H-benzo[7]annulen-6-one

Iodobenzene (6.42 g), m-chloroperoxybenzoic acid (7.80 g) and p-toluenesulfonic acid (6.0 g) were sequentially added to 1,1,1,3,3,3-hexafluoro-2-propanol/methylene chloride solution (1:6, 70 mL). The mixture was stirred for 30 minutes. Thereafter, water (12 mL) and the compound (6.57 g) prepared in Example 10 were added to the mixture at 0° C. The reaction mixture was stirred for 30 minutes and quenched with an aqueous saturated sodium bicarbonate solution. The mixture was extracted with ethyl acetate, and washed with saturated saline. The organic layer was dried with anhydrous sodium sulfate, and concentrated under reduced pressure. The obtained residue was purified by silica gel column chromatography (hexane:ethyl acetate=100:0→80:20) to give the title compound (5.5 g) having the following physical properties.

$^1$H-NMR (CDCl$_3$): δ 7.45-7.32, 7.13, 6.89, 6.79, 5.08, 3.73, 3.10-3.05, 2.54, 2.01-1.92.

Example 12: Methyl 1-[1-(benzyloxy)-6,7,8,9-tetrahydro-5H-benzo[7]annulen-6-yl]-3-azetidinecarboxylate A procedure for a purpose similar to that for Example 1 was carried out by using the compound (1.02 g) prepared in Example 11 and methyl azetidine-3-carboxylate hydrochloride (700 mg) to give the title compound (820 mg) having the following physical properties.

MS (M+H): 366.

Example 13: Methyl 1-(1-hydroxy-6,7,8,9-tetrahydro-5H-benzo[7]annulen-6-yl)-3-azetidinecarboxylate A mixture solution of the compound (820 mg) prepared in Example 12 and 10% palladium-carbon (400 mg) in ethyl acetate/methanol (1:1, 20 mL) was stirred at room temperature for 16 hours under hydrogen atmosphere. The reaction mixture was filtered through diatomaceous earth, and the filtrate was concentrated under reduced pressure to give the title compound (590 mg) having the following physical properties.

$^1$H-NMR (CDCl$_3$): δ 6.94, 6.68, 6.61, 3.69, 3.70-3.64, 3.58-3.53, 3.34-2.23, 3.19-3.13, 2.76-2.63, 2.50-2.43, 2.19-2.14, 1.96-1.94, 1.50-1.42, 1.38-1.32.

Example 14: Methyl 1-[1-({(2E)-3-[4-(trifluoromethyl)phenyl]-2-propen-1-yl}oxy)-6,7,8,9-tetrahydro-5H-benzo[7]annulen-6-yl]-3-azetidinecarboxylate To a THF (1.0 mL) solution of the compound (30 mg) prepared in Example 13, the compound (26.4 mg) prepared in Example 5, azodicarbonyldipiperidine (55.0 mg) and tributylphosphine were added, and the mixture was stirred at room temperature for 16 hours. The reaction mixture was concentrated under reduced pressure and the obtained residue was purified by silica gel column chromatography (hexane:ethyl acetate=40:60→0:100) to give the title compound (44.3 mg) having the following physical properties.

$^1$H-NMR (CDCl$_3$): δ 7.57, 7.50, 7.05, 6.80-6.70, 6.51, 4.68, 3.70, 3.70-3.59, 3.59-3.48, 3.40-3.20, 2.80-2.60, 2.49, 2.15, 2.02-1.85, 1.70-1.15.

Example 15: 1-[1-({(2E)-3-[4-(Trifluoromethyl)phenyl]-2-propen-1-yl}oxy)-6,7,8,9-tetrahydro-5H-benzo[7]annulen-6-yl]-3-azetidinecarboxylic Acid

[Chemical Formula 22]

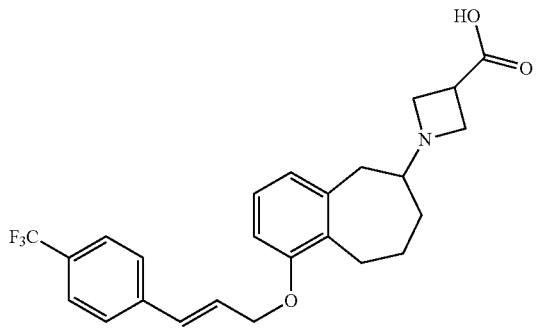

A procedure for a purpose similar to that for Example 3 was carried out by using the compound prepared in Example 14 to give the title compound having the following physical properties.

(LC-MS/ELSD): (Retention time: 0.95 minutes, Condition A);

MS (M+H): 446.

Example 15 (1): 1-[1-({(2E)-3-[4-(trifluoromethyl)phenyl]-2-propen-1-yl}oxy)-6,7,8,9-tetrahydro-5H-benzo[7]annulen-6-yl]-3-pyrrolidinecarboxylic Acid A procedure for a purpose similar to that for Example 12→Example 13→Example 14→Example 15 was carried out by using the compound prepared in Example 11 and a corresponding amine derivative in place of methyl azetidine-3-carboxylate hydrochloride to give the title compound having the following physical properties.

(LC-MS/ELSD): (Retention time: 0.96 minutes, Condition A);

MS (M+H): 460.

Example 16: Ethyl 4-(6-methoxy-1,2,4,5-tetrahydro-3H-3-benzazepin-3-yl)butanoate To a solution of 6-methoxy-2,3,4,5-tetrahydro-1H-3-benzazepine (1.0 g) (CAS registry number: 90047-53-3) in DMF (15 mL), potassium carbonate (1.56 g) and ethyl 4-bromobutanoate (1321 mg) were added, and the mixture was stirred at room temperature for 16 hours. The reaction mixture was poured into water, and extracted with ethyl acetate two times. The organic layer was washed with saturated saline, dried with anhydrous magnesium sulfate, and concentrated under reduced pressure. The obtained residue was purified by silica gel column chromatography (hexane:ethyl acetate=60:40→10:90) to give the title compound (1.37 g) having the following physical properties.

$^1$H-NMR (CDCl$_3$):δ 7.07, 6.74, 6.72, 4.13, 3.79, 3.05-2.95, 2.94-2.86, 2.65-2.54, 2.51, 2.37, 1.83, 1.26.

Example 17: Ethyl 4-(6-hydroxy-1,2,4,5-tetrahydro-3H-3-benzazepin-3-yl)butanoate To a dichloromethane (23 mL) solution of the compound (1.37 g) prepared in Example 16, 1M borontribromide solution in dichloromethane (9.4 mL) was added at 0° C., and the mixture was stirred at 0° C. for 2 hours. To the reaction mixture, 1M borontribromide solution in dichloromethane (4.7 mL) was added, and the mixture was stirred at 0° C. for another 2 hours. The reaction mixture was poured into an aqueous saturated sodium bicarbonate solution, and extracted with ethyl acetate two times. The organic layer was washed with water and saturated saline, dried with anhydrous magnesium sulfate, and concentrated under reduced pressure. The obtained residue was purified by silica gel column chromatography (hexane:ethyl acetate=70:30→20:70) to give the title compound (591 mg) having the following physical properties.

$^1$H-NMR (CDCl$_3$):δ 6.95, 6.68, 6.62, 4.13, 3.05-2.95, 2.95-2.85, 2.71-2.58, 2.53, 2.35, 1.86, 1.26.

Example 18: 4-[6-({(2E)-3-[4-(Trifluoromethyl)phenyl]-2-propen-1-yl}oxy)-1,2,4,5-tetrahydro-3H-3-benzazepin-3-yl]butanoic Acid

[Chemical Formula 23]

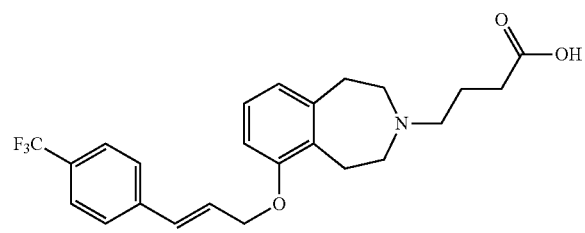

A procedure for a purpose similar to that for Example 14→Example 3 was carried out by using the compound prepared in Example 17 and the compound prepared in Example 5 to give the title compound having the following physical properties.

(LC-MS/ELSD): (Retention time: 0.92 minutes, Condition A);
MS (M+H): 434.

Example 18 (1)-18 (45)

A procedure for a purpose similar to that for Example 16→Example 17→Example 18 was carried out by using 6-methoxy-2,3,4,5-tetrahydro-1H-3-benzazepine or a corresponding dihydroisoquinoline compound, ethyl 4-bromobutanoate or a corresponding ester halide compound, and any one compound selected from the following (i) to (iv) ((i) the compound prepared in Example 5, (ii) the compound prepared in Example 6, (iii) the compound prepared in Example 8, (iv) a corresponding alcohol compound in place of (i) to (iii)) to give the following compounds of Examples.

Example 18 (1): 4-{5-[2-(2-naphthyl)ethoxy]-3,4-dihydro-2(1H)-isoquinolinyl}butanoic Acid trifluoroacetate (LC-MS/ELSD): (Retention time: 0.81 minutes, Condition B);
MS (M+H): 390.

Example 18 (2): 4-[8-({(2E)-3-[4-(Trifluoromethyl)phenyl]-2-propen-1-yl}oxy)-3,4-dihydro-2(1H)-isoquinolinyl]butanoic Acid trifluoroacetate (LC-MS/ELSD): (Retention time: 0.83 minutes, Condition B);
MS (M+H): 420.

Example 18 (3): 4-[5-{[(2E)-3-(4-Isopropylphenyl)-2-propen-1-yl]oxy}-3,4-dihydro-2(1H)-isoquinolinyl]butanoic Acid (LC-MS/ELSD): (Retention time: 0.96 minutes, Condition A);
MS (M+H): 394.

Example 18 (4): 4-[5-({(2E)-3-[4-(Difluoromethoxy)phenyl]-2-propen-1-yl}oxy)-3,4-dihydro-2(1H)-isoquinolinyl]butanoic Acid (LC-MS/ELSD): (Retention time: 0.86 minutes, Condition A);
MS (M+H): 418.

Example 18 (5): 4-[5-({(2E)-3-[4-(2,2,2-Trifluoroethyl)phenyl]-2-propen-1-yl}oxy)-3,4-dihydro-2(1H)-isoquinolinyl]butanoic Acid (LC-MS/ELSD): (Retention time: 0.93 minutes, Condition A);
MS (M+H): 434.

Example 18 (6): 4-[5-{[(2E)-3-{4-[1-(Trifluoromethyl)cyclopropyl]phenyl}-2-propen-1-yl]oxy}-3,4-dihydro-2(1H)-isoquinolinyl]butanoic Acid (LC-MS/ELSD): (Retention time: 0.98 minutes, Condition A);
MS (M+H): 460.

Example 18 (7): [6-({(2E)-3-[4-(Trifluoromethyl)phenyl]-2-propen-1-yl}oxy)-1,2,4,5-tetrahydro-3H-3-benzazepin-3-yl]acetic Acid (LC-MS/ELSD): (Retention time: 0.91 minutes, Condition A);
MS (M+H): 406.

Example 18 (8): 3-[6-({(2E)-3-[4-(Trifluoromethyl)phenyl]-2-propen-1-yl}oxy)-1,2,4,5-tetrahydro-3H-3-benzazepin-3-yl]propanoic Acid (LC-MS/ELSD): (Retention time: 0.92 minutes, Condition A);
MS (M+H): 420.

Example 18 (9): 5-[6-({(2E)-3-[4-(Trifluoromethyl)phenyl]-2-propen-1-yl}oxy)-1,2,4,5-tetrahydro-3H-3-benzazepin-3-yl]pentanoic Acid (LC-MS/ELSD): (Retention time: 0.93 minutes, Condition A);
MS (M+H): 448.

Example 18 (10): 4-(6-{2-[4-(Trifluoromethyl)phenoxy]ethoxy}-1,2,4,5-tetrahydro-3H-3-benzazepin-3-yl)butanoic Acid (LC-MS/ELSD): (Retention time: 0.80 minutes, Condition B);
MS (M+H): 438;
$^1$H-NMR (CDCl$_3$):δ 7.57, 7.13, 7.01, 6.82, 6.78, 4.41-4.27, 3.30-2.52, 1.92-1.81.

Example 18 (11): 4-[6-(3-Phenylpropoxy)-1,2,4,5-tetrahydro-3H-3-benzazepin-3-yl]butanoic Acid (LC-MS/ELSD): (Retention time: 0.79 minutes, Condition B);
MS (M+H): 368;
$^1$H-NMR (CD$_3$OD):δ 7.34-7.24, 7.23-7.15, 7.09, 6.76-6.70, 3.94, 3.60-2.50, 2.19-2.04, 1.96-1.86.

Example 18 (12): 4-[6-(2-Phenoxyethoxy)-1,2,4,5-tetrahydro-3H-3-benzazepin-3-yl]butanoic Acid (LC-MS/ELSD): (Retention time: 0.71 minutes, Condition B);
MS (M+H): 370;
$^1$H-NMR (CD$_3$OD):δ 7.35-7.27, 7.13, 7.01-6.89, 6.84, 6.76, 4.31, 3.32-2.70, 2.63-2.56, 1.97-1.85.

Example 18 (13): 2,2-Dimethyl-4-[6-(3-phenylpropoxy)-1,2,4,5-tetrahydro-3H-3-benzazepin-3-yl]butanoic Acid (LC-MS/ELSD): (Retention time: 0.91 minutes, Condition A);
MS (M+H): 396.

Example 18 (14): 4-[6-(3-Cyclohexylpropoxy)-1,2,4,5-tetrahydro-3H-3-benzazepin-3-yl]butanoic Acid (LC-MS/ELSD): (Retention time: 0.95 minutes, Condition B);
MS (M+H): 374.

Example 18 (15): 4-[6-({(2E)-3-[4-(Difluoromethoxy)phenyl]-2-propen-1-yl}oxy)-1,2,4,5-tetrahydro-3H-3-benzazepin-3-yl]butanoic Acid (LC-MS/ELSD): (Retention time: 0.82 minutes, Condition B);
MS (M+H): 432.

Example 18 (16): 4-[6-(1,2,3,4-Tetrahydro-2-naphthalenylmethoxy)-1,2,4,5-tetrahydro-3H-3-benzazepin-3-yl]butanoic Acid (LC-MS/ELSD): (Retention time: 0.86 minutes, Condition B);
MS (M+H): 394.

Example 18 (17): 4-[6-(2,3-Dihydro-1H-inden-2-ylmethoxy)-1,2,4,5-tetrahydro-3H-3-benzazepin-3-yl]butanoic Acid (LC-MS/ELSD): (Retention time: 0.82 minutes, Condition B);
MS (M+H): 380.

Example 18 (18): 4-{6-[2-(1-Naphthyl)ethoxy]-1,2,4,5-tetrahydro-3H-3-benzazepin-3-yl}butanoic Acid

[Chemical Formula 24]

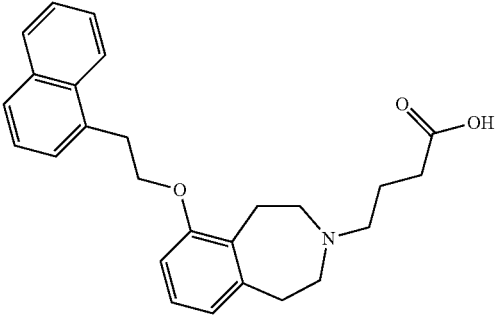

(LC-MS/ELSD): (Retention time: 0.83 minutes, Condition B);
MS (M+H): 404;
$^1$H-NMR (CD$_3$OD):δ 8.07, 7.87, 7.79-7.72, 7.56-7.39, 7.04, 6.75-6.66, 4.28, 3.56, 3.30-2.50, 2.00-1.86.

Example 18 (19): 4-{6-[2-(2-Naphthyl)ethoxy]-1,2,4,5-tetrahydro-3H-3-benzazepin-3-yl}butanoic Acid (LC-MS/ELSD): (Retention time: 0.83 minutes, Condition B);
MS (M+H): 404.

Example 18 (20): 4-{6-[2-(1,2,3,4-Tetrahydro-1-naphthalenyl)ethoxy]-1,2,4,5-tetrahydro-3H-3-benzazepin-3-yl}butanoic Acid (LC-MS/ELSD): (Retention time: 0.90 minutes, Condition B);
MS (M+H): 408.

Example 18 (21): rel-4-(6-{[(1R,2S)-2-Phenylcyclopropyl]methoxy}-1,2,4,5-tetrahydro-3H-3-benzazepin-3-yl)butanoic Acid (LC-MS/ELSD): (Retention time: 0.85 minutes, Condition A);
MS (M+H): 380.

Example 18 (22): 4-[6-(2-Phenylethoxy)-1,2,4,5-tetrahydro-3H-3-benzazepin-3-yl]butanoic Acid (LC-MS/ELSD): (Retention time: 0.81 minutes, Condition A);
MS (M+H): 354.

Example 18 (23): 4-[6-(4-Phenylbutoxy)-1,2,4,5-tetrahydro-3H-3-benzazepin-3-yl]butanoic Acid (LC-MS/ELSD): (Retention time: 0.90 minutes, Condition A);
MS (M+H): 382.

Example 18 (24): 4-{6-[(5-Phenylpentyl)oxy]-1,2,4,5-tetrahydro-3H-3-benzazepin-3-yl}butanoic Acid (LC-MS/ELSD): (Retention time: 0.94 minutes, Condition A);
MS (M+H): 396.

Example 18 (25): 4-[6-(Bicyclo[4.2.0]octa-1,3,5-trien-7-ylmethoxy)-1,2,4,5-tetrahydro-3H-3-benzazepin-3-yl]butanoic Acid (LC-MS/ELSD): (Retention time: 0.83 minutes, Condition A);
MS (M+H): 366.

Example 18 (26): 4-{6-[2-(Bicyclo[4.2.0]octa-1,3,5-trien-7-yl)ethoxy]-1,2,4,5-tetrahydro-3H-3-benzazepin-3-yl}butanoic Acid (LC-MS/ELSD): (Retention time: 0.88 minutes, Condition A);
MS (M+H): 380.

Example 18 (27): 3-{6-[2-(1-Naphthyl)ethoxy]-1,2,4,5-tetrahydro-3H-3-benzazepin-3-yl}propanoic Acid (LC-MS/ELSD): (Retention time: 0.83 minutes, Condition B);
MS (M+H): 390.

Example 18 (28): 4-(6-Butoxy1,2,4,5-tetrahydro-3H-3-benzazepin-3-yl)butanoic Acid (LC-MS/ELSD): (Retention time: 0.77 minutes, Condition A);
MS (M+H): 306.

Example 18 (29): 4-[6-(Pentyloxy)-1,2,4,5-tetrahydro-3H-3-benzazepin-3-yl]butanoic Acid (LC-MS/ELSD): (Retention time: 0.82 minutes, Condition A);
MS (M+H): 320.

Example 18 (30): 4-[6-(Hexyloxy)-1,2,4,5-tetrahydro-3H-3-benzazepin-3-yl]butanoic Acid (LC-MS/ELSD): (Retention time: 0.87 minutes, Condition A);
MS (M+H): 334.

Example 18 (31): 4-[6-(Heptyloxy)-1,2,4,5-tetrahydro-3H-3-benzazepin-3-yl]butanoic Acid (LC-MS/ELSD): (Retention time: 0.93 minutes, Condition A);
MS (M+H): 348.

Example 18 (32): 4-[6-(Octyloxy)-1,2,4,5-tetrahydro-3H-3-benzazepin-3-yl]butanoic Acid

[Chemical Formula 25]

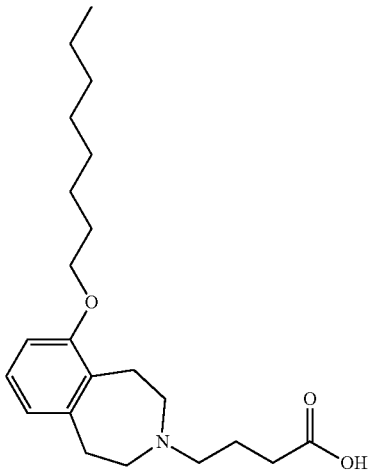

(LC-MS/ELSD): (Retention time: 0.97 minutes, Condition A);
MS (M+H): 362;
$^1$H-NMR (CD$_3$OD):δ 7.06, 6.80, 6.71, 3.89, 3.75-3.55, 3.18-2.86, 2.84-2.65, 2.37, 2.03-1.88, 1.76-1.62, 1.47-1.34, 1.34-1.13, 0.81.

Example 18 (33): 4-{6-[(4,5,5-Trifluoro-4-penten-1-yl)oxy]-1,2,4,5-tetrahydro-3H-3-benzazepin-3-yl}butanoic Acid (LC-MS/ELSD): (Retention time: 0.78 minutes, Condition A);
MS (M+H): 372.

Example 18 (34): 4-{6-[(5-Methylhexyl)oxy]-1,2,4,5-tetrahydro-3H-3-benzazepin-3-yl}butanoic Acid (LC-MS/ELSD): (Retention time: 0.91 minutes, Condition A);
MS (M+H): 347.

Example 18 (35): 4-{6-[3-(3-Pyridinyl)propoxy]-1,2,4,5-tetrahydro-3H-3-benzazepin-3-yl}butanoic Acid (LC-MS/ELSD): (Retention time: 0.53 minutes, Condition A);
MS (M+H): 368.

Example 18 (36): 4-{6-[3-(2-Pyridinyl)propoxy]-1,2,4,5-tetrahydro-3H-3-benzazepin-3-yl}butanoic Acid (LC-MS/ELSD): (Retention time: 0.51 minutes, Condition A);
MS (M+H): 368.

Example 18 (37): 4-[6-(2-Cyclobutylethoxy)-1,2,4,5-tetrahydro-3H-3-benzazepin-3-yl]butanoic Acid (LC-MS/ELSD): (Retention time: 0.83 minutes, Condition A);
MS (M+H): 331.

Example 18 (38): 4-{6-[3-(4-Fluorophenyl)propoxy]-1,2,4,5-tetrahydro-3H-3-benzazepin-3-yl}butanoic Acid (LC-MS/ELSD): (Retention time: 0.85 minutes, Condition A);
MS (M+H): 385;
$^1$H-NMR (CD$_3$OD):δ 7.24, 7.19, 7.02, 6.89, 6.84, 4.01, 3.89-3.62, 3.29-3.18, 3.16-2.75, 2.83, 2.50, 2.18-2.01.

Example 18 (39): 4-{6-[3-(1,3-Thiazol-5-yl)propoxy]-1,2,4,5-tetrahydro-3H-3-benzazepin-3-yl}butanoic Acid (LC-MS/ELSD): (Retention time: 0.63 minutes, Condition A);
MS (M+H): 374.

Example 18 (40): 4-{6-[3-(1,2-Thiazol-4-yl)propoxy]-1,2,4,5-tetrahydro-3H-3-benzazepin-3-yl}butanoic Acid (LC-MS/ELSD): (Retention time: 0.71 minutes, Condition A);
MS (M+H): 374.

Example 18 (41): 4-{6-[3-(2-Oxo-1-pyrrolidinyl)propoxy]-1,2,4,5-tetrahydro-3H-3-benzazepin-3-yl}butanoic Acid (LC-MS/ELSD): (Retention time: 0.60 minutes, Condition A);
MS (M+H): 374.

Example 18 (42): 4-{6-[3-(tetrahydro-2H-pyran-4-yl)propoxy]-1,2,4,5-tetrahydro-3H-3-benzazepin-3-yl}butanoic Acid

[Chemical Formula 26]

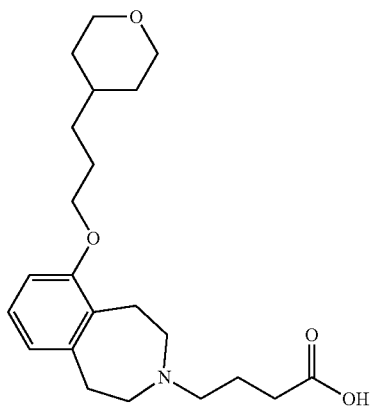

(LC-MS/ELSD): (Retention time: 0.75 minutes, Condition A);
MS (M+H): 375;
$^1$H-NMR (CD$_3$OD):δ 7.19, 6.93, 6.84, 4.01, 3.95, 3.87-3.66, 3.44, 3.30-3.18, 3.18-2.96, 2.94-2.77, 2.49, 2.14-1.99, 1.91-1.79, 1.69, 1.65-1.52, 1.51-1.39, 1.29.

Example 18 (43): 4-(6-{2-[2-(Trifluoromethyl)phenyl]ethoxy}-1,2,4,5-tetrahydro-3H-3-benzazepin-3-yl)butanoic Acid (LC-MS/ELSD): (Retention time: 0.87 minutes, Condition A);
MS (M+H): 421;
$^1$H-NMR (CD$_3$OD):δ 7.72, 7.63-7.55, 7.45, 7.19, 6.94, 6.85, 4.33-4.21, 3.82-3.62, 3.29-2.99, 2.98-2.71, 2.49, 2.13-1.97.

Example 18 (44): 4-(6-{[(4S)-4-Methylhexyl]oxy}-1,2,4,5-tetrahydro-3H-3-benzazepin-3-yl)butane (LC-MS/ELSD): (Retention time: 0.91 minutes, Condition A);
MS (M+H): 347.

Example 18 (45): 4-{6-[3-(1-methyl-1H-pyrazole-4-yl)propoxy]-1,2,4,5-tetrahydro-3H-3-benzazepin-3-yl}butanoic Acid (LC-MS/ELSD): (Retention time: 0.64 minutes, Condition A);
MS (M+H): 371.

Example 19: 2-Methyl-2-propanyl 6-hydroxy-1,2,4,5-tetrahydro-3H-3-benzazepine-3-carboxylate To a solution of 6-methoxy-2,3,4,5-tetrahydro-1H-3-benzazepine (200 mg) in dichloromethane (5.0 mL), 1M boron tribromide solution in dichloromethane (2.54 mL) was added at 0° C., and the mixture was stirred at 0° C. for 5 hours. The reaction mixture was cooled to −78° C., methanol was added thereto, and the reaction mixture was stirred at −78° C. for 15 minutes. The reaction mixture was warmed to room temperature, stirred foe a while and concentrated under reduced pressure. To a THF (5.0 mL) suspension of the obtained residue, 2N sodium hydroxide (1.41 mL) and di-tert-butyldicarbonate (265 mg) were added, and the mixture was stirred at room temperature for 6 hours. The reaction mixture was poured into 1N hydrochloric acid, and extracted with ethyl acetate two times. The organic layer was washed with saturated saline, dried with anhydrous magnesium sulfate, and concentrated under reduced pressure. The obtained residue was purified by silica gel column chromatography (hexane:ethyl acetate=100:0→75:25) to give the title compound (286 mg) having the following physical properties.
$^1$H-NMR (CDCl$_3$):δ 6.97, 6.71, 6.64, 4.91, 3.60-3.50, 3.02-2.94, 2.93-2.86, 1.48.

Example 20: 2-Methyl-2-propanyl-6-({(2E)-3-[4-(trifluoromethyl)phenyl]-2-propen-1-yl}oxy)-1,2,4,5-tetrahydro-3H-3-benzazepine-3-carboxylate A procedure for a purpose similar to that for Example 14 was carried out by using the compound prepared in Example 19 and the compound prepared in Example 5 to give the title compound (286 mg) having the following physical properties.
$^1$H-NMR (CDCl$_3$):δ 7.58, 7.51, 7.08, 7.83-6.71, 6.51, 4.70, 3.62-3.48, 3.12-3.00, 2.98-2.86, 1.47.

Example 21: 6-({(2E)-3-[4-(Trifluoromethyl)phenyl]-2-propen-1-yl}oxy)-2,3,4,5-tetrahydro-1H-3-benzazepine hydrochloride To a methanol (1.0 mL) solution of the compound (190 mg) prepared in Example 20, ethyl acetate (1.0 mL) suspension, 4N hydrochloric acid (6.0 mL) was added at 0° C., and the mixture was stirred at room temperature for 1.5 hours. The reaction mixture was concentrated under reduced pressure to give the title compound (157 mg) having the following physical properties.

$^1$H-NMR (DMSO-d$_6$):δ 9.05, 7.71, 7.14, 6.97, 6.89-6.79, 6.69, 4.75, 3.26-2.99.

Example 22 (1): Methyl 3-[6-({(2E)-3-[4-(trifluoromethyl)phenyl]-2-propen-1-yl}oxy)-1,2,4,5-tetrahydro-3H-benzazepin-3-yl]cyclobutanecarboxylate (Low Polar Form)

Example 22 (2): Methyl 3-[6-({(2E)-3-[4-(trifluoromethyl)phenyl]-2-propen-1-yl}oxy)-1,2,4,5-tetrahydro-3H-benzazepin-3-yl]cyclobutanecarboxylate (High Polar Form)

A procedure for a purpose similar to that for Example 1 was carried out by using the compound prepared in Example 21 and Methyl 3-oxocyclobutanecarboxylate (CAS registry number: 695-95-4) in place of Methyl azetidine-3-carboxylate hydrochloride to give the title compound having the following physical properties.

(Example 22 (1)): $^1$H-NMR (CDCl$_3$):δ 7.58, 7.51, 7.06, 6.78, 6.77, 6.73, 6.51, 4.68, 3.68, 3.15-3.00, 2.95-2.85, 2.80-2.67, 2.51-2.28, 2.25-2.11.

(Example 22 (2)): $^1$H-NMR (CDCl$_3$):δ 7.58, 7.51, 7.07, 6.79, 6.78, 6.74, 6.51, 4.69, 3.71, 3.20-2.82, 2.55-2.18.

Example 23 (1): 3-[6-({(2E)-3-[4-(Trifluoromethyl)phenyl]-2-propen-1-yl}oxy)-1,2,4,5-tetrahydro-3H-3-benzazepin-3-yl]cyclobutanecarboxylic acid (Low Polar Form)

Example 23 (2): 3-[6-({(2E)-3-[4-(Trifluoromethyl)phenyl]-2-propen-1-yl}oxy)-1,2,4,5-tetrahydro-3H-3-benzazepin-3-yl]cyclobutanecarboxylic acid (High Polar Form)

[Chemical Formula 27]

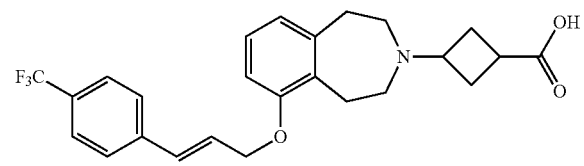

A procedure for a purpose similar to that for Example 3 was carried out by using the compound prepared in Example 22 (1) or Example 22 (2) to give the title compound having the following physical properties, respectively.

Example 23 (1): (LC-MS/ELSD): (Retention time: 0.85 minutes, Condition B);
MS (M+H): 446.

Example 23 (2): (LC-MS/ELSD): (Retention time: 0.86 minutes, Condition B);
MS (M+H): 446.

Example 23 (3)-23 (9)

A procedure for a purpose similar to that for Example 19→Example 20→Example 21→Example 22(1) or 22(2)→Example 23(1) or 23(2) was carried out by using 6-methoxy-2,3,4,5-tetrahydro-1H-3-benzazepine, the compound prepared in Example 5 or a corresponding alcohol compound and 3-oxocyclobutanecarboxylate or a corresponding cyclic ketone compound to give the following compounds of Examples.

Example 23 (3): rel-(1R,2R)-2-{[6-({(2E)-3-[4-(Trifluoromethyl)phenyl]-2-propen-1-yl}oxy)-1,2,4,5-tetrahydro-3H-3-benzazepin-3-yl]methyl}cyclopropanecarboxylic Acid (LC-MS/ELSD): (Retention time: 0.85 minutes, Condition B);
MS (M+H): 446.

Example 23 (4): rel-(1R,2S)-2-{[6-({(2E)-3-[4-(trifluoromethyl)phenyl]-2-propen-1-yl}oxy)-1,2,4,5-tetrahydro-3H-3-benzazepin-3-yl]methyl}cyclopropanecarboxylic Acid (LC-MS/ELSD): (Retention time: 0.86 minutes, Condition B);
MS (M+H): 446.

Example 23 (5): 1-Methyl-3-[6-({(2E)-3-[4-(trifluoromethyl)phenyl]-2-propen-1-yl}oxy)-1,2,4,5-tetrahydro-3H-3-benzazepin-3-yl]cyclobutanecarboxylic Acid (High Polar Form)

(LC-MS/ELSD): (Retention time: 0.94 minutes, Condition A);
MS (M+H): 460.

Example 23 (6): 1-Methyl-3-[6-({(2E)-3-[4-(trifluoromethyl)phenyl]-2-propen-1-yl}oxy)-1,2,4,5-tetrahydro-3H-3-benzazepin-3-yl]cyclobutanecarboxylic Acid (Low Polar Form)

(LC-MS/ELSD): (Retention time: 0.95 minutes, Condition A);
MS (M+H): 460.

Example 23 (7): 3-[6-({(2E)-3-[4-(Trifluoromethyl)phenyl]-2-propen-1-yl}oxy)-1,2,4,5-tetrahydro-3H-3-benzazepin-3-yl]cyclopentanecarboxylic Acid (LC-MS/ELSD): (Retention time: 0.93 minutes, Condition A);
MS (M+H): 460.

Example 23 (8): 3-{6-[2-(1-Naphthyl)ethoxy]-1,2,4,5-tetrahydro-3H-3-benzazepin-3-yl}cyclobutanecarboxylic Acid (Low Polar Form)

(LC-MS/ELSD): (Retention time: 0.88 minutes, Condition A);
MS (M+H): 416.

Example 23 (9): 3-{6-[2-(1-Naphthyl)ethoxy]-1,2,4,5-tetrahydro-3H-3-benzazepin-3-yl}cyclobutanecarboxylic Acid (High Polar Form)

(LC-MS/ELSD): (Retention time: 0.87 minutes, Condition A);
MS (M+H): 416.

Example 24: 2-Methyl-2-propanyl-6-hydroxy-7-(hydroxymethyl)-1,2,4,5-tetrahydro-3H-3-benzazepine-3-carboxylate To a water (2.0 mL) suspension of the compound (132 mg) prepared in Example 19, butanol (0.4 mL) and disodium 3,7-dioxide-2,4,6,8,9-pentaoxa-1,3,5,7-tetraborabicyclo[3,3,1]nonane (404 mg) were added, and the mixture was stirred at 60° C. for 10 minutes. To the reaction mixture, 37% aqueous formaldehyde solution (1.0 mL) was added, and the mixture was stirred at 60° C. for 72 hours. The reaction mixture was poured into 1N hydrochloric acid and extracted with ethyl acetate two times. The organic layer was washed with water and saturated saline, dried with anhydrous magnesium sulfate, and concentrated under reduced pressure. The obtained residue was purified by silica gel column chromatography (hexane:ethyl acetate=90:10→50:50) to give the title compound (80.1 mg) having the following physical properties.
$^1$H-NMR (CDCl$_3$):δ 7.68, 6.78, 6.62, 4.84, 3.58-3.48, 3.05-2.98, 2.90-2.82, 2.23, 1.48.

Example 25: 2-Methyl-2-propanyl 6-hydroxy-7-Methyl-1,2,4,5-tetrahydro-3H-3-benzazepine-3-carboxylate To a methanol (3.0 mL) solution of the compound (78 mg) prepared in Example 24, palladiumplatinum (ASCA-2 (trade name), 15 mg) was added, and the mixture was stirred at room temperature for 1 hour under hydrogen atmosphere. The reaction mixture was filtered through Celite (trade name) and the filtrate was concentrated under reduced pressure. The obtained residue was purified by silica gel column chromatography (hexane:ethyl acetate=100:0→75:25) to give the title compound (71.2 mg) having the following physical properties.
$^1$H-NMR (CDCl$_3$):δ 6.88, 6.63, 4.65, 3.60-3.50, 3.03-2.95, 2.91-2.82, 2.23, 1.47.

Example 26: 2-Methyl-2-propanyl 7-Methyl-6-(3-phenylpropoxy)-1,2,4,5-tetrahydro-3H-3-benzazepin-3-carboxylate A procedure for a purpose similar to that for Example 14 was carried out by using the compound prepared in Example 25 and 3-phenyl-1-propanol in place of the compound prepared in Example 5 to give the title compound having the following physical properties.
$^1$H-NMR (CDCl$_3$):δ 7.35-7.17, 6.93, 6.79, 3.69, 3.57-3.42, 2.94, 2.89-2.79, 2.25, 2.14, 1.49.

Example 27: 7-Methyl-6-(3-phenylpropoxy)-2,3,4,5-tetrahydro-1H-3-benzazepine hydrochloride A procedure for a purpose similar to that for Example 21 was carried out by using the compound prepared in Example 26 to give the title compound having the following physical properties.
$^1$H-NMR (CD$_3$OD):δ 7.32-7.14, 7.02, 6.88, 3.70, 3.29-3.21, 3.21-3.11, 3.11-3.03, 2.85, 2.23, 2.14.

Example 28: Ethyl 4-[7-Methyl-6-(3-phenylpropoxy)-1,2,4,5-tetrahydro-3H-3-benzazepin-3-yl]butanoate A procedure for a purpose similar to that for Example 16 was carried out by using the compound prepared in Example 27 and ethyl 4-bromobutanoate to give the title compound having the following physical properties.
$^1$H-NMR (CD$_3$OD):δ 7.34-7.15, 6.90, 6.76, 4.13, 3.69, 3.02-2.92, 2.92-2.78, 2.68-2.51, 2.48, 2.35, 2.24, 2.13, 1.84, 1.26.

Example 29: 4-[7-Methyl-6-(3-phenylpropoxy)-1,2,4,5-tetrahydro-3H-3-benzazepin-3-yl]butanoic Acid

[Chemical Formula 28]

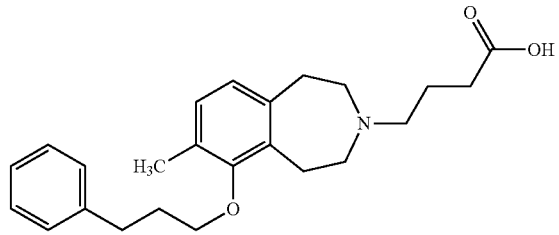

A procedure for a purpose similar to that for Example 3 was carried out by using the compound prepared in Example 28 to give the title compound having the following physical properties.
(LC-MS/ELSD): (Retention time: 0.87 minutes, Condition A);
MS (M+H): 382.

Example 30: Ethyl 4-(6-{[(trifluoromethyl)sulfonyl]oxy}-1,2,4,5-tetrahydro-3H-3-benzazepin-3-yl)butanoate Diisopropylethylamine (0.374 mL) and N,N-bis(trifluoromethylsulfonyl)aniline (580 mg) were added to a dichloromethane (1.5 mL) solution of the compound (150 mg) prepared in Example 17 at 0° C., and the mixture was stirred at room temperature for 16 hours. The reaction mixture was poured into water, and extracted with ethyl acetate two times. The organic layer was washed with saturated saline, dried with anhydrous magnesium sulfate, and concentrated under reduced pressure. The obtained residue was purified by silica gel column chromatography (hexane:ethyl acetate=85:15→55:45) to give the title compound (179 mg) having the following physical properties.
$^1$H-NMR (CDCl$_3$):δ 7.20-7.05, 4.14, 3.04-2.92, 2.70-2.60, 2.51, 2.38, 1.84, 1.27.

Example 31: Ethyl 4-[6-(4-phenyl-1-butyn-1-yl)-1,2,4,5-tetrahydro-3H-3-benzazepin-3-yl]butanoate 4-phenyl-1-butyne (38.2 mg), trimethylamine (0.27 mL), copper iodide (1.9 mg) and bis(triphenylphosphine)palladiumdichloride (6.9 mg) were added to a DMF (0.5 mL) solution of the compound (40 mg) prepared in Example 30, and the mixture was stirred at 50° C. for 16 hours. The reaction mixture was purified by silica gel column chromatography (hexane:ethyl acetate=90:10→50:50) and preparative TLC (hexane:ethyl acetate=60:40) to give the title compound (7.5 mg) having the following physical properties.
$^1$H-NMR (CDCl$_3$):δ 7.37-7.18, 7.03-6.96, 4.14, 3.12-3.05, 2.96-2.84, 2.72, 2.65-2.51, 2.48, 2.36, 1.84, 1.27.

Example 32: Ethyl 4-[6-(4-phenylbutyl)-1,2,4,5-tetrahydro-3H-3-benzazepin-3-yl]butanoate A procedure for a purpose similar to that for Example 25 was carried out by using the compound prepared in Example 31 to give the title compound having the following physical properties.
$^1$H-NMR (CDCl$_3$):δ 7.29-7.23, 7.20-7.14, 7.03-6.90, 4.14, 2.92-2.85, 2.66-2.57, 2.53, 2.46, 2.35, 1.83, 1.76-1.44, 1.26.

Example 33: 4-[6-(4-Phenylbutyl)-1,2,4,5-tetrahydro-3H-3-benzazepin-3-yl]butanoic Acid

[Chemical Formula 29]

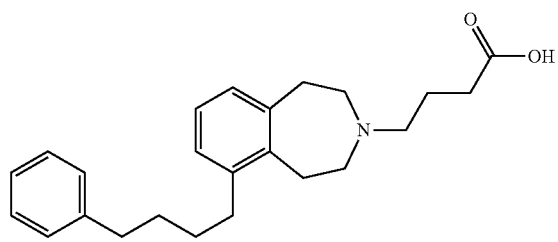

A procedure for a purpose similar to that for Example 3 was carried out by using the compound prepared in Example 32 to give the title compound having the following physical properties.
(LC-MS/ELSD): (Retention time: 0.88 minutes, Condition B);
MS (M+H): 366.

Example 34: Sodium [1-(Hydroxymethyl)cyclopropyl]acetate

A ethanol (10 mL) and water (1.0 mL) solution of 2-[1-(hydroxymethyl)cyclopropyl]acetonitrile (1.0 g) (CAS registry number: 152922-71-9) was treated with sodium hydroxide (1.4 g), and the obtained mixture was stirred at 90° C. for 16 hours. The reaction mixture was concentrated under reduced pressure to give the title compound (1.2 g) having the following physical properties.
$^1$H-NMR (DMSO-d$_6$):δ 3.17, 2.04, 3.30-0.22, 0.21-0.18.

Example 35: Ethyl [1-(Hydroxymethyl)cyclopropyl]acetate

Sulfuric acid (0.5 mL) was added to a ethanol (10 mL) solution of the compound (1.2 g) prepared in Example 34, and the mixture was stirred at 90° C. for 2 hours. The reaction mixture was poured into ice water, and extracted with ethyl acetate. The organic layer was washed with water and saturated saline, dried with anhydrous magnesium sulfate, and concentrated under reduced pressure to give the title compound (900 mg) having the following physical properties.
$^1$H-NMR (DMSO-d$_6$):δ 4.52, 4.03, 3.25, 2.32, 1.75, 0.47.

Example 36: Ethyl [1-(Bromomethyl)cyclopropyl]acetate

Tetrabromomethane (1.2 g) and triphenylphosphine (1.0 g) were added to a methylene chloride (6 mL) solution of the compound (500 mg) prepared in Example 35 at 0° C., and the mixture was stirred at room temperature for 2 hours. The reaction mixture was diluted with water, and extracted with ethyl acetate. The organic layer was washed with saturated saline, dried with anhydrous magnesium sulfate, filtered, and the filtrate was concentrated under reduced pressure. The obtained residue was purified by silica gel column chromatography (ethyl acetate:hexane=100:0→70:30) to give the title compound (450 mg) having the following physical properties.
$^1$H-NMR (DMSO-d$_6$):δ 4.07, 3.60, 2.43, 1.18, 0.43 3.60, 2.469-0.64.

Example 37: [1-({6-[2-(1-Naphthyl)ethoxy]-1,2,4,5-tetrahydro-3H-3-benzazepin-3-yl}methyl)cyclopropyl]acetic Acid

[Chemical Formula 30]

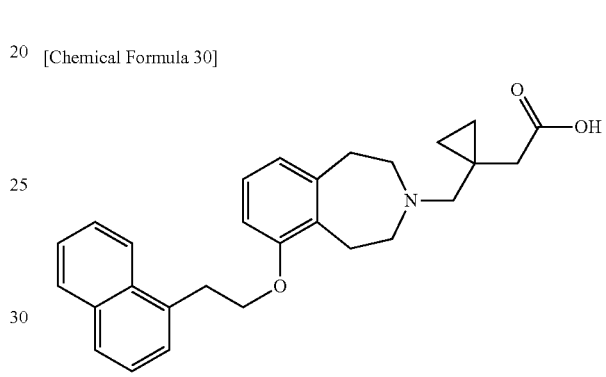

A procedure for a purpose similar to that for Example 18 was carried out by using the compound prepared in Example 36 and a corresponding alcohol compound in place of the compound prepared in Example 5 to give the title compound having the following physical properties.
(LC-MS/ELSD): (Retention time: 0.87 minutes, Condition B);
MS (M+H): 430.

Example 38: 5-Methoxy-3,4-dihydro-2(1H)-naphthalenone oxime

Sodium acetate (2.79 g) and hydroxylamine hydrochloride (2.37 g) were added to a ethanol (60 mL) solution of 5-methoxytetralin-2-one (2.00 g), and the mixture was stirred at 70° C. for 1.5 hours. Water was added to the reaction mixture, and ethanol was reduced by concentration under reduced pressure. Saturated saline was added to the resulting mixture, and the mixture was extracted twice with ethyl acetate. The organic layer was dried with anhydrous magnesium sulfate, and concentrated under reduced pressure. The obtained residue was purified by silica gel column chromatography (hexane:ethyl acetate=100:0→70:30) to give the title compound (1.77 g) having the following physical properties.
$^1$H-NMR (CDCl$_3$):δ 7.16, 6.80, 6.72, 3.83, 3.82, 2.89, 2.52.

Example 39: 6-Methoxy-1,2,4,5-tetrahydro-3H-2-benzazepin-3-one

A THF (1.5 mL) suspension of the compound (1.00 g) prepared in Example 38 was added to a mixture solution of thionyl chloride (10 mL) and THF (5.0 mL) at 0° C., and the mixture was stirred at 0° C. for 1.5 hours. The reaction mixture was poured into water and extracted twice with ethyl acetate. The organic layer was washed with an aqueous saturated sodium bicarbonate solution and saturated saline, dried with anhydrous magnesium sulfate, and concentrated under reduced pressure. The obtained residue was purified by silica gel column chromatography (hexane:ethyl acetate=20:80→0:100-ethyl acetate:methanol=80:20) to give the title compound (500 mg) having the following physical properties.

$^1$H-NMR (CDCl$_3$):δ 7.14, 6.83, 6.71, 6.14, 4.38, 3.83, 3.06, 2.82.

Example 40:
6-Methoxy-2,3,4,5-tetrahydro-1H-2-benzazepine

To a THF (6.0 mL) suspension of lithium aluminium hydride (164 mg), a THF (15.0 mL) suspension of the compound (550 mg) prepared in Example 39 was slowly added at 80° C., and the mixture was stirred at 80° C. for 15 minutes. The reaction mixture was cooled to room temperature, added an aqueous saturated sodium sulfate solution and THF, and the mixture was stirred at room temperature for 30 minutes. Anhydrous magnesium sulfate was added to the reaction mixture, and the mixture was filtered. The filtrate was concentrated under reduced pressure to give the title compound (433 mg) having the following physical properties.

$^1$H-NMR (CDCl$_3$):δ 7.07, 6.77, 6.75, 3.93, 3.80, 3.21, 3.04, 1.66.

Example 41: 4-(Benzyloxy)-1-indanone

Potassium carbonate (3.5 g) was added to a acetonitrile (40 mL) solution of 4-hydroxy-1-indanone (1.5 g) (CAS registry number: 40731-98-4) and benzylbromide (1.45 mL). The reaction mixture was refluxed for 3 hours, filtered, and the filtrate was concentrated under vacuum to give the title compound (2.2 g) having the following physical properties.

$^1$H-NMR (CDCl$_3$):δ 7.48-7.28, 7.09, 5.17, 3.10, 2.73-2.65.

Example 42: 4-(Benzyloxy)-1-indanol

Sodium borohydride (0.64 g) was added to a methanol (20 mL) and THF (20 mL) solution of the compound (2.0 g) prepared in Example 41 at 0° C. The reaction mixture was stirred at room temperature for 4 hours, and quenched with saturated ammonium chloride. The reaction mixture was extracted with ethyl acetate, dried with anhydrous magnesium sulfate, filtered, and the filtrate was concentrated under vacuum to give the title compound (1.8 g) having the following physical properties.

$^1$H-NMR (CDCl$_3$):δ 7.44-7.32, 7.23-7.19, 7.04, 6.82, 5.27-5.25, 5.11, 3.08-3.05, 2.83-2.81, 2.52-2.48, 2.00-1.94, 1.69.

Example 43: 7-(Benzyloxy)-1H-indene

P-toluenesulfonic acid (7 mg) was added to a toluene (40 mL) solution of the compound (1.0 g) prepared in Example 42, and the mixture was heated under reflux, and water was removed by azeotropic distillation using Dean-Stark apparatus for 4 hours. The reaction mixture was quenched with an aqueous saturated sodium bicarbonate solution, extracted with ethyl acetate, dried with anhydrous magnesium sulfate, filtered, and the filtrate was concentrated under vacuum. The obtained residue was purified by silica gel column chromatography (hexane:ethyl acetate=100:0→20:80) to give the title compound (0.6 g) having the following physical properties.

$^1$H-NMR (CDCl$_3$):δ 7.36-7.30, 7.25-7.21, 7.07, 6.87-6.85, 6.79, 6.58-6.56, 5.18, 3.42.

Example 44: 4-(Benzyloxy)-1,2-indanediol

Water (2.5 mL) and N-methylmorpholine N-oxide (632 mg) were added to an acetone (10 mL) solution of the compound (600 mg) prepared in Example 43. After 5 minutes stirred, a tert-butylalcohol (1.0 mL) solution of osmium tetroxide (34 mg) was added dropwise to the mixture, and the mixture was stirred at room temperature for 2 hours. The solvent was concentrated under reduced pressure, and the obtained residue was dissolved in ethyl acetate, and the solution was washed with 1N aqueous sodium thiosulfate solution and saturated saline. The organic layer was dried with anhydrous sodium sulfate, filtered, and the filtrate was concentrated to give the title compound (450 mg) having the following physical properties.

$^1$H-NMR (CDCl$_3$):δ 7.41-7.30, 7.23, 7.06, 6.84, 5.09, 5.02, 4.54-4.52, 3.15-3.10, 3.00-2.95, 2.52, 2.36.

Example 45:
4-(Benzyloxy)-1,3-dihydro-2H-inden-2-one

P-toluenesulfonic acid (5 mg) was added to a toluene (50 mL) solution of the compound (750 mg) prepared in Example 44, and the mixture was heated under reflux, and water was removed by azeotropic distillation using Dean-Stark apparatus for 4 hours. The reaction mixture was stirred at room temperature for 4 hours, quenched with an aqueous saturated sodium bicarbonate solution, extracted with ethyl acetate, dried with anhydrous magnesium sulfate, filtered, and the filtrate was concentrated under vacuum. The obtained residue was purified by silica gel column chromatography (hexane:ethyl acetate=100:0-20:80) to give the title compound (400 mg) having the following physical properties.

ESI-MS m/z 280 [C$_{16}$H$_{14}$O$_2$+H+CH$_3$CN]+.

Example 46: Methyl 1-[4-(benzyloxy)-2,3-dihydro-1H-inden-2-yl]-3-azetidinecarboxylate A procedure for a purpose similar to that for Example 1 was carried out by using the compound prepared in Example 45 and methyl azetidine-3-carboxylate hydrochloride to give the title compound having the following physical properties.

$^1$H-NMR (CDCl$_3$):δ 7.40-7.31, 7.09, 6.81, 6.70, 5.07, 3.70, 3.61-3.58, 3.32-3.24, 3.00-2.93, 2.75-2.71.

Example 47: Methyl 1-(4-hydroxy-2,3-dihydro-1H-inden-2-yl)-3-azetidinecarboxylate A procedure for a purpose similar to that for Example 13 was carried out by using the compound prepared in Example 46 to give the title compound having the following physical properties.

$^1$H-NMR (CDCl$_3$):δ 7.01, 6.76, 6.56, 3.71, 3.64-3.60, 3.35-3.27, 3.00-2.87, 2.75-2.64.

Example 48: 1-[4-(2-Phenylethoxy)-2,3-dihydro-1H-inden-2-yl]-3-azetidinecarboxylic Acid

[Chemical Formula 31]

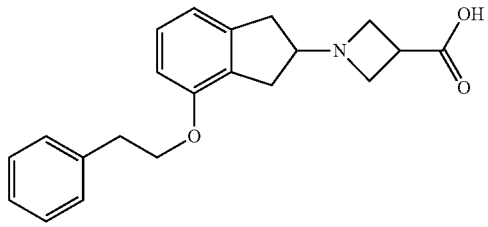

A procedure for a purpose similar to that for Example 14→Example 3 was carried out by using the compound prepared in Example 47 and 2-phenylethanol in place of the compound prepared in Example 5 to give the title compound having the following physical properties.
(LC-MS/ELSD): (Retention time: 0.78 minutes, Condition A);
MS (M+H): 338.

Example 48 (1)-48 (2)

A procedure for a purpose similar to that for Example 47 was carried out by using the compound prepared in Example 47 and corresponding alcohol derivative in place of 2-phenylethanol to give the title compound having the following physical properties.

Example 48 (1): 1-[4-(3-Phenylpropoxy)-2,3-dihydro-1H-inden-2-yl]-3-azetidinecarboxylic Acid (LC-MS/ELSD): (Retention time: 0.83 minutes, Condition A);
MS (M+H): 352.

Example 48 (2): 1-[4-(4-Phenylbutoxy)-2,3-dihydro-1H-inden-2-yl]-3-azetidinecarboxylic Acid (LC-MS/ELSD): (Retention time: 0.87 minutes, Condition A);
MS (M+H): 366.

Example 49: 5-[6-({(2E)-3-[4-(Trifluoromethyl)phenyl]-2-propen-1-yl}oxy)-1,3,4,5-tetrahydro-2H-2-benzazepin-2-yl]pentanoic Acid

[Chemical Formula 32]

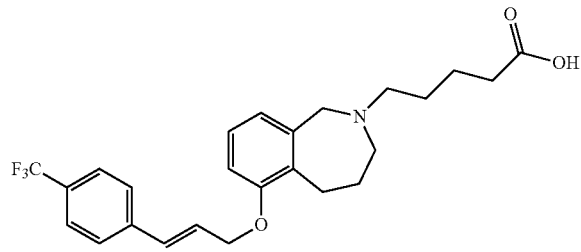

A procedure for a purpose similar to that for Example 16→Example 17→Example 18 was carried out by using the compound prepared in Example 40, ethyl 5-bromopentanoate in place of ethyl 4-bromobutanoate, and the compound prepared in Example 5 to give the title compound having the following physical properties.
(LC-MS/ELSD): (Retention time: 0.92 minutes, Condition A);
MS (M+H): 448.

Example 50 (1): Methyl 1-{8-[2-(1-naphthyl)ethoxy]-1,2,3,4-tetrahydro-2-naphthalenyl}-3-azetidinecarboxylate (the First Peak)

Example 50 (2): Methyl 1-{8-[2-(1-naphthyl)ethoxy]-1,2,3,4-tetrahydro-2-naphthalenyl}-3-azetidinecarboxylate (the Second Peak)

The optical resolution of the compound prepared in Example 2 (1) was carried out by using SFC (Supercritical Fluid Chromatography): {column:DAICEL CHIRALPAK IB (column length: 10×250 mm); flow rate: 30 mL/min; column temperature: 35° C.; mobile phase: carbon dioxide:methanol:diethylamine=85:15:0.015; detector:UV to give the title compound having the following physical properties.
$^1$H-NMR (CDCl$_3$):δ 8.10, 7.86, 7.75, 7.56-7.36, 7.02, 6.67, 6.62, 4.30, 3.74, 3.65-3.52, 3.42-3.24, 2.88-2.61, 2.46-2.34, 2.15, 1.89-1.77, 1.50-1.33.
(the first peak) Retention time: 4.52 minutes;
(the second peak) Retention time: 5.94 minutes.

Example 51 (1): (−)-1-{8-[2-(1-Naphthyl)ethoxy]-1,2,3,4-tetrahydro-2-naphthalenyl}-3-azetidinecarboxylic Acid Example 50 (2): (+)-1-{8-[2-(1-Naphthyl)ethoxy]-1,2,3,4-tetrahydro-2-naphthalenyl}-3-azetidinecarboxylic Acid

[Chemical Formula 33]

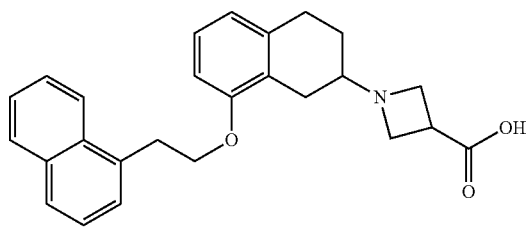

A procedure for a purpose similar to that for Example 3 was carried out by using the compound prepared in Example 50 (1) or Example 50 (2) to give the title compound having the following physical properties. Further, Example 51 (1) and Example 51 (2) were derived from Example 50 (1) and Example 50 (2) respectively.
(LC-MS/ELSD): (Retention time: 0.85 minutes, Condition B);
MS (M+H): 402.
Example 51 (1): [α]$_D$=−52.7 (DMF, c=1.0);
Example 51 (2): [α]$_D$=+53.4 (DMF, c=1.0).

Example 52: 1-[8-(Hexyloxy)-1,2,3,4-tetrahydro-2-naphthalenyl]-3-azetidinecarboxylic Acid A procedure for a purpose similar to that for Example 1→Example 17 was carried out by using 8-methoxy-3,4- dihydronaphthalen-2(1H)-one in place of 5-hydroxy-3,4-dihydronaphthalene-2(1H)-one, and a procedure for a purpose similar to that for Example 14→Example 3 was carried out by using 1-hexanol in place of the compound prepared in Example 5 to give the title compound having the following physical properties.

(LC-MS/ELSD): (Retention time: 0.88 minutes, Condition A);
MS (M+H): 332.

Example 52 (1)-(8)

A procedure for a purpose similar to that for Example 52 was carried out by using a corresponding alcohol compound in place of 1-hexanol to give the following compounds of Examples.

Example 52 (1): 1-[8-(Heptyloxy)-1,2,3,4-tetrahydro-2-naphthalenyl]-3-azetidinecarboxylic Acid (LC-MS/ELSD): (Retention time: 0.92 minutes, Condition A);
MS (M+H): 346.

Example 52 (2): 1-[8-(Octyloxy)-1,2,3,4-tetrahydro-2-naphthalenyl]-3-azetidinecarboxylic Acid

[Chemical Formula 34]

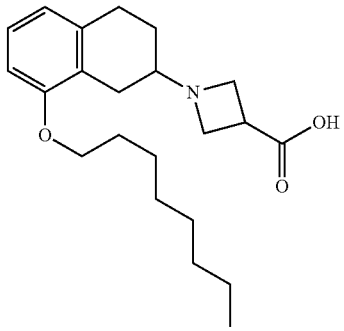

(LC-MS/ELSD): (Retention time: 0.97 minutes, Condition A);
MS (M+H): 360;
$^1$H-NMR (CD$_3$OD):δ 7.10, 6.74, 6.71, 4.36-4.18, 4.04-3.91, 3.63-3.49, 3.45-3.34, 3.17, 2.96-2.79, 2.41, 2.23-2.10, 1.85-1.71, 1.70-1.58, 1.58-1.44, 1.44-1.23, 0.90.

Example 52 (3): 1-[8-(Nonyloxy)-1,2,3,4-tetrahydro-2-naphthalenyl]-3-azetidinecarboxylic Acid (LC-MS/ELSD): (Retention time: 1.02 minutes, Condition A);
MS (M+H): 374;
$^1$H-NMR (CD$_3$OD):δ 7.10, 6.74, 6.71, 4.36-4.18, 4.04-3.91, 3.63-D):δ 7.10, 6.74, 6.71, 4.36-4.18, 4.04-3.91, 3.63 10, 1.85-1.71, 1.70-1.58, 1.58-1.44, 1.44-1.23, 0.89.

Example 52 (4): 1-[8-(Decyloxy)-1,2,3,4-tetrahydro-2-naphthalenyl]-3-azetidinecarboxylic Acid (LC-MS/ELSD): (Retention time: 1.07 minutes, Condition A);
MS (M+H): 388.

Example 52 (5): 1-[8-(Undecyloxy)-1,2,3,4-tetrahydro-2-naphthalenyl]-3-azetidinecarboxylic Acid (LC-MS/ELSD): (Retention time: 1.12 minutes, Condition A);
MS (M+H): 402.

Example 52 (6): 1-{8-[3-(1,2-Thiazol-4-yl)propoxy]-1,2,3,4-tetrahydro-2-naphthalenyl}-3-azetidinecarboxylic Acid (LC-MS/ELSD): (Retention time: 0.73 minutes, Condition A);
MS (M+H): 373

Example 52 (7): 1-{8-[3-(Tetrahydro-2H-pyran-4-yl)propoxy]-1,2,3,4-tetrahydro-2-naphthalenyl}-3-azetidinecarboxylic Acid

[Chemical Formula 35]

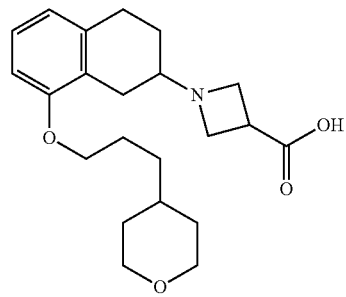

(LC-MS/ELSD): (Retention time: 0.76 minutes, Condition A);
MS (M+H): 374;
$^1$H-NMR (CD$_3$OD):δ 7.12, 6.77, 6.74, 4.36-4.15, 4.07-3.91, 3.58-D):δ 7.12, 6.77, 6.74, 4.36-4.15, 4.07-3.91, 3.58 thalenyl}-3-azetidinecarboxylic acid. 70-1.58, 1.58-, 2.46 1.22.

Example 52 (8): 1-[8-(3-Cyclohexylpropoxy)-1,2,3,4-tetrahydro-2-naphthalenyl]-3-azetidinecarboxylic Acid (LC-MS/ELSD): (Retention time: 0.97 minutes, Condition A);
MS (M+H): 372;
$^1$H-NMR (CD$_3$OD):δ 7.12, 6.76, 6.74, 4.37-4.18, 4.07-3.91, 3.63-D):δ 7.12, 6.76, 6.74, 4.37-4.18, 4.07-3.91, 3.63 carboxylic acid-3-azetidinecarboxylic acid. 70-1.58, 1.58-0.89.

Example 53: Methyl 1-(5-Chloro-8-hydroxy-1,2,3,4-tetrahydronaphthalen-2-yl)azetidine-3-carboxylate trifluoroacetate (1/1)

A DMF (0.5 mL) solution of N-chlorosuccinimide (51 mg) was added to a DMF (0.5 mL) solution of methyl 1-(8-hydroxy-1,2,3,4-tetrahydronaphthalen-2-yl)azetidine-3-carboxylate (100 mg) under ice cooling, and the mixture was stirred at room temperature for 16 hours. The reaction mixture was poured into an aqueous saturated sodium bicarbonate solution, and extracted twice with ethyl acetate. The organic layer was washed with saturated saline, dried with anhydrous magnesium sulfate, and concentrated under reduced pressure. The obtained residue was purified by silica gel column chromatography (hexane:ethyl acetate=60: 40→20:80), and then, purified by reversed phase liquid chromatography (0.1% trifluoroacetic acid (TFA)-containing water/0.1% TFA-containing acetonitrile) to give the title compound (10 mg) having the following physical properties.

$^1$H-NMR (DMSO-d6):δ 10.45-10.20, 9.89, 7.11, 6.69, 4.60-4.15, 3.85-3.47, 3.09-2.95, 2.67-:δ 10.45-10.2 2.23, 2.20-2.03, 1.68-1.42.

Example 54: 1-{5-Chloro-8-[2-(naphthalen-1-yl) ethoxy]-1,2,3,4-tetrahydronaphthalen-2-yl}azetidine-3-carboxylic Acid trifluoroacetate (1:1)

A procedure for a purpose similar to that for Example 14 was carried out by using the compound prepared in Example 53 in place of the compound prepared in Example 13, and 2-(naphthalen-1-yl)ethanol in place of the compound prepared in Example 5. 2N sodium hydroxide (0.05 mL) was added to a methanol (0.1 mL) and dimethoxyethane (0.1 mL) solution of the resulting compound (8 mg), and the mixture was stirred at room temperature for 4 hours. 2N hydrochloric acid (0.05 mL) was added to the reaction mixture, and the reaction mixture was purified by reversed phase liquid chromatography (0.1% TFA-containing water/ 0.1% TFA-containing acetonitrile) to give the title compound (3.2 mg) having the following physical properties.

(LC-MS/ELSD): (Retention time: 0.92 minutes, Condition A);

MS (M+H): 435.

Biological Experimental Examples will be described hereinbelow, and the effects of the compound of the present invention were confirmed based on the experimental methods.

Biological Experimental Example 1: Measurement of the Inhibitory Action of the Compound of the Present Invention on Binding of [$^{33}$P]-S1P to S1P$_5$ (EDG-8)

A reaction was carried out in a 96-well microplate by using membrane fractions of Chinese hamster ovary (CHO) cells each of which was made to overexpress human S1P$_1$ (EDG-1) or human S1P$_5$ gene respectively, in an amount of the membrane fraction of 1 mg protein/mL. To each of the wells, 100 μL of a vehicle (DMSO) solution or a two-fold concentration-ligand solution each of which was diluted with Binding Buffer (50 mmol/L, Tris pH 7.5, 5 mmol/L, MgCl$_2$, 0.5% BSA and Complete EDTA free (1 tablet/50 mL)), and 50 μL of 0.16 nmol/L [$^{33}$P]-S1P (manufactured by American Radiolabeled Chemicals, Inc.) diluted with Binding Buffer were added. Thereafter, the membrane fraction solutions (50 μL) was added to the wells and the reaction was carried out at room temperature for 60 minutes. After the reaction, suction filtration was carried out by using a 96-well UNIFILTER, and the 96-well microplate was washed with Wash Buffer (50 mmol/L, Tris pH 7.5, 0.5% BSA) (150 mL), and thereafter, was dried at 60° C. for 45 minutes. MicroScint (trade name) 20 (50 μL/well) was added and the plate was covered with TopSeal-A, and thereafter, the radioactivity was measured by using Top-Count (manufactured by PerkinElmer Inc.).

[Results]

The compound of the present invention exhibited the inhibitory activity (IC50 value) as shown in the following table on binding of [$^{33}$P]-S1P to S1P$_5$. In addition, the binding activities of the compounds of the present invention to S1P$_1$ of [$^{33}$P]-S1P are shown in Table 1. Further, the symbols in the Table 1 represent the value of IC50 is A: 1 nM or more and less than 100 nM, B: 100 nM or more and less than 1000 nM, C: 1 μM to 3 μM, D: >10 μM and E: >30 μM, respectively. As a result, it was found that all the compounds of the present invention had high S1P$_5$ receptor binding activity, and a selective S1P$_5$ receptor binding activity against S1P$_1$ receptor binding activity.

TABLE 1

| Example No. | S1P$_5$ binding activity (IC50) | S1P$_1$ binding activity (IC50) |
| --- | --- | --- |
| Example 18 (1) | C | E |
| Example 18 (2) | C | E |
| Example 18 (3) | C | E |
| Example 18 (4) | C | E |
| Example 18 (8) | B | D |
| Example 49 | C | E |
| Example 3 (1) | C | E |
| Example 18 (10) | A | D |
| Example 3 (3) | B | E |
| Example 18 (14) | B | D |
| Example 18 (16) | B | D |
| Example 18 (18) | A | D |
| Example 18 (22) | B | D |
| Example 18 (24) | A | D |
| Example 18 (26) | B | D |
| Example 3 (4) | A | D |
| Example 23 (8) | A | D |
| Example 29 | A | D |
| Example 51 (1) | A | D |
| Example 51 (2) | A | D |
| Example 37 | B | D |
| Example 48 | B | E |
| Example 18 (32) | B | D |
| Example 18 (42) | B | D |

Biological Example 2: Evaluation of S1P$_5$ Receptor Agonist Activities of the Compound of the Present Invention by Monitoring the Concentration of Produced Intracellular Cyclic AMP CHO cells which were made to overexpress human S1P$_5$ (EDG-8) gene were cultured in Ham's F12 Medium (manufactured by Gibco-BRL) containing 10% FBS (fetal bovine serum), penicillin/streptomycin and geneticin (0.25 mg/mL). The medium was removed from the cultured cells, the cultured cells were washed once with phosphate-buffered saline, and the cultured cells were treated with a vehicle (DMSO) solution or a compound solution each of which was diluted with Buffer (Hanks' balanced salt solution containing 20 mmol/L HEPES, 0.1 or 0.2% BSA, 1 mmol/L IBMX and 5 μmol/L forskolin) at 37° C. for 30 minutes. Thereafter, the cultured cells were washed once with phosphate-buffered saline, lysis of the cells, and the concentration of cyclic AMP in the cell lysate were measured by using cAMP Assay Kit (Cisbio Bioassays).

[Results]

As a result, it was found that the compound of the present invention had a selective S1P$_5$ receptor modulatory activity. Further, the symbol in the Table 2 represents the value of EC50 is A: 1 nM or more and less than 100 nM.

TABLE 2

| Example No. | S1P$_5$ receptor agonist activity (EC50) |
|---|---|
| Example 18 (11) | A |
| Example 18 (18) | A |
| Example 3 (5) | A |

PREPARATION EXAMPLES

Preparation Example 1

The following components were mixed in a conventional manner and compressed to give 10,000 tablets each containing 10 mg of the active component.
4-{5-[2-(2-naphthyl)ethoxy]-3,4-dihydro-2(1H)-isoquinolinyl}butanoic acid trifluoroacetate . . . 100 g
Carboxymethyl cellulose calcium (a disintegrating agent) . . . 20 g
Magnesium stearate (a lubricant) . . . 10 g
Microcrystalline cellulose . . . 870 g Preparation Example 2

The following components were mixed in a conventional manner. Thereafter, the mixture was filtered through a dust filter, and 5 ml aliquots were charged into ampules. The ampules were heat sterilized by an autoclave to give 10,000 ampules each containing 20 mg of the active component.
1-[5-({(2E)-3-[4-(trifluoromethyl)phenyl]-2-propen-1-yl}oxy)-1,2,3,4-tetrahydro-2-naphthalenyl]-3-pyrrolidinecarboxylic acid . . . 200 g
Mannitol . . . 20 g
Distilled water . . . 50 L

INDUSTRIAL APPLICABILITY

The compound of the present invention has a selective S1P$_5$ receptor binding activity and modulates the function of an S1P$_5$ receptor, and therefore, is useful for treating S1P$_5$-mediated disease, for example, neurodegenerative disease and the like.

The invention claimed is:
1. A compound represented by general formula (I-1):

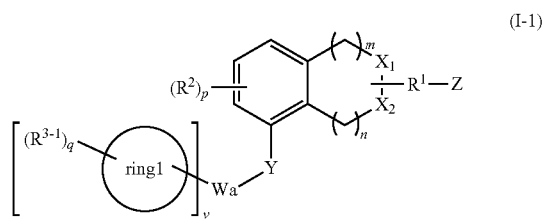

(I-1)

wherein, $X^1$ and $X^2$ each represent independently a CH$_2$ or an NH, provided that $X^1$ and $X^2$ are not represent NH at the same time,
Y represents (1) —CH$_2$—, (2) —NH—, (3) —S— or (4) —O—,
$W^A$ represents (1) a C1-12 alkylene group, (2) a C2-12 alkenylene group, (3) a C2-12 alkynylene group, (4) —C1-12 alkylene-O—, (5) —C2-12 alkenylene-O—, (6) —C2-12 alkynylene-O—, (7) —C1-12 alkylene-ring2-, (8) —C2-12 alkenylene-ring2- or (9) —C2-12 alkynylene-ring2-, wherein, an alkylene group, an alkenylene group and an alkynylene group may be substituted with one to five halogen atoms,
$R^1$ represents (1) -L-, (2) -L-ring3- or (3) -L-NR$^{13}$—,
$R^2$ represents (1) a halogen atom, (2) a C1-4 alkyl group, (3) a C1-4 haloalkyl group, or (4) a C1-4 haloalkoxy group,
$R^{3-1}$ represents (1) a halogen atom, (2) a C1-4 alkyl group, (3) a C1-4 haloalkyl group, (4) a C1-4 alkoxy group, (5) a C1-4 haloalkoxy group, (6) a nitrile group, (7) —S—C1-4 alkyl group, (8) —S—C1-4 haloalkyl group or (9) an oxo group, provided that the C1-4 alkyl group or the C1-4 haloalkyl group represented by $R^{3-1}$ is branched chain, C1-2 alkyl groups branched from the same carbon atom may be taken together with a carbon atom to which they are bound, to form a C3-4 saturated carbocyclic ring,
$R^{13}$ represents (1) a hydrogen atom or (2) a C1-4 alkyl group,
L represents a group represented by general formula

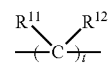

wherein, $R^{11}$ and $R^{12}$ each represent independently a hydrogen atom or a C1-4 alkyl group, or $R^{11}$ and $R^{12}$ may be taken together with a carbon atom to which they are bound, to form a C3-7 carbocyclic ring, and t represents an integer of 1 to 6,
Z represents (1) a carboxyl group which may be substituted with a C1-8 alkyl group, (2) a hydroxamic acid group which may be substituted with a C1-8 alkyl group, (3) a sulfonic acid group which may be substituted with a C1-8 alkyl group, (4) a boronic acid group which may be substituted with a C1-8 alkyl group, (5) a carbamoyl group which may be substituted with a C1-8 alkyl group, (6) a sulfamoyl group which may be substituted with a C1-8 alkyl group, (7) a sulfoximine group which may be substituted with a C1-8 alkyl group or (8) a tetrazolyl group,
ring 1 represents a C3-10 carbocyclic ring,
ring 2 represents (1) a C3-7 carbocyclic ring or (2) a 3- to 7-membered heterocyclic ring,
ring 3 represents (1) a C3-7 carbocyclic ring which may be substituted with a C1-4 alkyl group or (2) a 3- to 7-membered heterocyclic ring which may be substituted with a C1-4 alkyl group,
m represents an integer of 0 to 2,
n represents an integer of 0 to 2,
p represents an integer of 0 to 3,
q represents an integer of 0 to 5,
v represents an integer of 0 to 1,
when p is 2 or more, a plurality of $R^2$s may be the same or different,
when q is 2 or more, a plurality of $R^{3-1}$s may be the same or different,
when t is 2 or more, a plurality of $R^{11}$s may be the same or different, and
when t is 2 or more, a plurality of $R^{12}$s may be the same or different, or a pharmaceutically acceptable salt thereof.

2. The compound according to claim 1, which is represented by the following general formula (I):

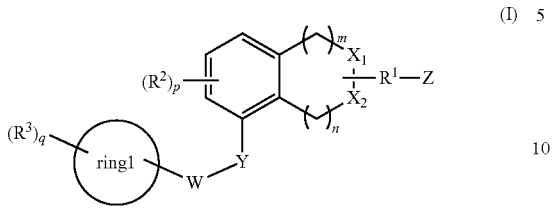

wherein, W represents (1) a C1-6 alkylene group, (2) a C2-6 alkenylene group, (3) a C2-6 alkynylene group, (4) a —C1-6 alkylene-O—, (5) a —C2-6 alkenylene-O—, (6) a —C2-6 alkynylene-O— or (7) a —C1-6 alkylene-ring2-, $R^3$ represents (1) a halogen atom, (2) a C1-4 alkyl group, (3) a C1-4 haloalkyl group, (4) a C1-4 alkoxy group, (5) a C1-4 haloalkoxy group, (6) a nitrile group, (7) a —S—C1-4 alkyl group, or (8) a —S—C1-4 haloalkyl group, provided that the C1-4 alkyl group or the C1-4 haloalkyl group represented by $R^3$ is branched chain, C1-2 alkyl groups branched from the same carbon atom may be taken together with a carbon atom to which they are bound, to form a C3-4 saturated carbocyclic ring, when q is 2 or more, a plurality of $R^3$s may be the same or different and other symbols have the same meanings as described in claim 1, or a pharmaceutically acceptable salt thereof.

3. The compound according to claim 1, wherein Y is —CH$_2$— or —O—, or a pharmaceutically acceptable salt thereof.

4. The compound according to claim 1, wherein ring 3 is a C3-7 saturated carbocyclic ring which may be substituted with a C1-4 alkyl group, or a 3- to 7-membered saturated heterocyclic ring which may be substituted with a C1-4 alkyl group, or a pharmaceutically acceptable salt thereof.

5. The compound according to claim 1, wherein Z is a carboxyl group which may be substituted with a C1-8 alkyl group, or a pharmaceutically acceptable salt thereof.

6. A pharmaceutical composition comprising
the compound represented by general formula (I-1) according to claim 1, or a pharmaceutically acceptable salt thereof; and
a pharmaceutically acceptable carrier.

7. A method for treating a S1P$_5$-mediated disease, comprising administering to a mammal in need thereof an effective amount of a compound represented by general formula (I-1), or a pharmaceutically acceptable salt thereof:

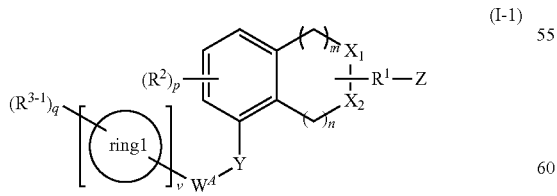

wherein, $X^1$ and $X^2$ each represent independently a CH$_2$ or an NH, provided that $X^1$ and $X^2$ are not represent NH at the same time, Y represents (1) —CH$_2$— (2) —NH—, (3) —S— or (4) —O—, $W^A$ represents (1) a C1-12 alkylene group, (2) a C2-12 alkenylene group, (3) a C2-12 alkynylene group, (4) —C1-12 alkylene-O—, (5) —C2-12 alkenylene-O—, (6) —C2-12 alkynylene-O—, (7) —C1-12 alkylene-ring2-, (8) —C2-12 alkenylene-ring2-, or (9) —C2-12 alkynylene-ring2-, wherein, an alkylene group, an alkenylene group and an alkynylene group may be substituted with one to five halogen atoms, $R^1$ represents (1) -L-, (2) -L-ring3- or (3) -L-NR$^{13}$-, $R^2$ represents (1) a halogen atom, (2) a C1-4 alkyl group, (3) a C1-4 haloalkyl group, or (4) a C1-4 haloalkoxy group, $R^{3-1}$ represents (1) a halogen atom, (2) a C1-4 alkyl group, (3) a C1-4 haloalkyl group, (4) a C1-4 alkoxy group, (5) a C1-4 haloalkoxy group, (6) a nitrile group, (7) —S—C1-4 alkyl group, (8) —S—C1-4 haloalkyl group or (9) an oxo group, provided that the C1-4 alkyl group or the C1-4 haloalkyl group represented by $R^{3-1}$ is branched chain, C1-2 alkyl groups branched from the same carbon atom may be taken together with a carbon atom to which they are bound, to form a C3-4 saturated carbocyclic ring, $R^{13}$ represents (1) a hydrogen atom or (2) a C1-4 alkyl group, L represents (1) a bond or (2) a group represented by general formula

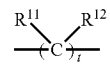

wherein, $R^{11}$ and $R^{12}$ each represent independently a hydrogen atom or a C1-4 alkyl group, or $R^{11}$ and $R^{12}$ may be taken together with a carbon atom to which they are bound, to form a C3-7 carbocyclic ring, and t represents an integer of 1 to 6, Z represents (1) a carboxyl group which may be substituted with a C1-8 alkyl group, (2) a hydroxy group which may be substituted with a C1-8 alkyl group, (3) a hydroxamic acid group which may be substituted with a C1-8 alkyl group, (4) a sulfonic acid group which may be substituted with a C1-8 alkyl group, (5) a boronic acid group which may be substituted with a C1-8 alkyl group, (6) a carbamoyl group which may be substituted with a C1-8 alkyl group, (7) a sulfamoyl group which may be substituted with a C1-8 alkyl group, (8) a sulfoximine group which may be substituted with a C1-8 alkyl group or (9) a tetrazolyl group, ring 1 represents (1) a C3-10 carbocyclic ring,
ring 2 represents (1) a C3-7 carbocyclic ring or (2) a 3- to 7-membered heterocyclic ring,
ring 3 represents (1) a C3-7 carbocyclic ring which may be substituted with a C1-4 alkyl group or (2) a 3- to 7-membered heterocyclic ring which may be substituted with a C1-4 alkyl group,
m represents an integer of 0 to 2,
n represents an integer of 0 to 2,
p represents an integer of 0 to 3,
q represents an integer of 0 to 5,
v represents an integer of 0 to 1,
when p is 2 or more, a plurality of $R^2$s may be the same or different,
when q is 2 or more, a plurality of $R^{3-1}$s may be the same or different,
when t is 2 or more, a plurality of $R^{11}$s may be the same or different, and when t is 2 or more, a plurality of $R^{12}$s may be the same or different, or a pharmaceutically acceptable salt thereof.

8. The compound according to claim 2, wherein Y is —CH$_2$— or —O—, or a pharmaceutically acceptable salt thereof.

9. The compound according to claim 2, wherein ring 3 is a C3-7 saturated carbocyclic ring which may be substituted with a C1-4 alkyl group, or a 3- to 7-membered saturated heterocyclic ring which may be substituted with a C1-4 alkyl group, or a pharmaceutically acceptable salt thereof.

10. The compound according to claim 2, wherein Z is a carboxyl group which may be substituted with a C1-8 alkyl group, or a pharmaceutically acceptable salt thereof.

11. The method according to claim 7, wherein the S1P$_5$-mediated disease is neurodegenerative disease, autoimmune disease, infection or cancer.

12. The method according to claim 11, wherein the neurodegenerative disease is schizophrenia, Binswanger's disease, multiple sclerosis, neuromyelitis optica, Alzheimer's disease, cognitive impairment, amyotrophic lateral sclerosis or spinocerebellar ataxia.

13. A method for treating a S1P$_5$-mediated disease according to claim 7, wherein the compound is represented by the following general formula (I);

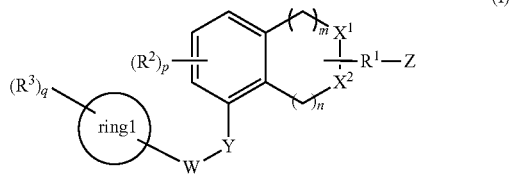

(I)

wherein, W represents (1) a C1-6 alkylene group, (2) a C2-6 alkenylene group, (3) a C2-6 alkynylene group, (4) a —C1-6 alkylene-O—, (5) a —C2-6 alkenylene-O—, (6) a —C2-6 alkynylene-O— or (7) a —C1-6 alkylene-ring2-, R$^3$ represents (1) a halogen atom, (2) a C1-4 alkyl group, (3) a C1-4 haloalkyl group, (4) a C1-4 alkoxy group, (5) a C1-4 haloalkoxy group, (6) a nitrile group, (7) a —S—C1-4 alkyl group, or (8) a —S—C1-4 haloalkyl group, provided that the C1-4 alkyl group or the C1-4 haloalkyl group represented by R$^3$ is branched chain, C1-2 alkyl groups branched from the same carbon atom may be taken together with a carbon atom to which they are bound, to form a C3-4 saturated carbocyclic ring, when q is 2 or more, a plurality of R$^3$s may be the same or different and other symbols have the same meanings as described in claim 7.

14. The method according to claim 13, wherein the S1P$_5$-mediated disease is neurodegenerative disease, autoimmune disease, infection or cancer.

15. The method according to claim 14, wherein the neurodegenerative disease is schizophrenia, Binswanger's disease, multiple sclerosis, neuromyelitis optica, Alzheimer's disease, cognitive impairment, amyotrophic lateral sclerosis or spinocerebellar ataxia.

16. A method for modulating a S1P$_5$ receptor, comprising contacting the S1P$_5$ receptor with the compound represented by general formula (I-1), or a pharmaceutically acceptable salt thereof:

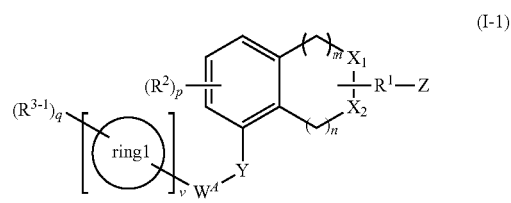

(I-1)

wherein, $X^1$ and $X^2$ each represent independently a CH$_2$ or an NH, provided that $X^1$ and $X^2$ are not represent NH at the same time, Y represents (1) —CH$_2$—, (2) —NH—, (3) —S— or (4) —O—, $W^A$ represents (1) a C1-12 alkylene group, (2) a C2-12 alkenylene group, (3) a C2-12 alkynylene group, (4) —C1-12 alkylene-O—, (5) —C2-12 alkenylene-O—, (6) —C2-12 alkynylene-O—, (7) —C1-12 alkylene-ring2-, (8) —C2-12 alkenylene-ring2- or (9) —C2-12 alkynylene-ring2-, wherein, an alkylene group, an alkenylene group and an alkynylene group may be substituted with one to five halogen atoms, $R^1$ represents (1) -L-, (2) -L-ring3- or (3) -L-NR$^{13}$, $R^2$ represents (1) a halogen atom, (2) a C1-4 alkyl group, (3) a C1-4 haloalkyl group, or (4) a C1-4 alkoxy group, $R^{3-1}$ represents (1) a halogen atom, (2) a C1-4 alkyl group, (3) a C1-4 haloalkyl group, (4) a C1-4 alkoxy group, (5) a C1-4 haloalkoxy group, (6) a nitrile group, (7) —S—C1-4 alkyl group, (8) —S—C1-4 haloalkyl group or (9) an oxo group, provided that the C1-4 alkyl group or the C1-4 haloalkyl group represented by $R^{3-1}$ is branched chain, C1-2 alkyl groups branched from the same carbon atom may be taken together with a carbon atom to which they are bound, to form a C3-4 saturated carbocyclic ring, $R^{13}$ represents (1) a hydrogen atom or (2) a C1-4 alkyl group, L represents (1) a bond or (2) a group represented by general formula

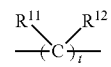

wherein, $R^{11}$ and $R^{12}$ each represent independently a hydrogen atom or a C1-4 alkyl group, or $R^{11}$ and $R^{12}$ may be taken together with a carbon atom to which they are bound, to form a C3-7 carbocyclic ring, and t represents an integer of 1 to 6, Z represents (1) a carboxyl group which may be substituted with a C1-8 alkyl group, (2) a hydroxy group which may be substituted with a C1-8 alkyl group, (3) a hydroxamic acid group which may be substituted with a C1-8 alkyl group, (4) a sulfonic acid group which may be substituted with a C1-8 alkyl group, (5)

a boronic acid group which may be substituted with a C1-8 alkyl group, (6) a carbamoyl group which may be substituted with a C1-8 alkyl group, (7) a sulfamoyl group which may be substituted with a C1-8 alkyl group, (8) a sulfoximine group which may be substituted with a C1-8 alkyl group or (9) a tetrazolyl group, ring 1 represents (1) a C3-10 carbocyclic ring, ring 2 represents (1) a C3-7 carbocyclic ring or (2) a 3- to 7-membered heterocyclic ring, ring 3 represents (1) a C3-7 carbocyclic ring which may be substituted with a C1-4 alkyl group or (2) a 3- to 7-membered heterocyclic ring which may be substituted with a C1-4 alkyl group, m represents an integer of 0 to 2, n represents an integer of 0 to 2, p represents an integer of 0 to 3, q represents an integer of 0 to 5, v represents an integer of 0 to 1, when p is 2 or more, a plurality of $R^2$s may be the same or different, when q is 2 or more, a plurality of $R^{3-1}$s may be the same or different, when t is 2 or more, a plurality of $R^{11}$s may be the same or different, and when t is 2 or more, a plurality of $R^{12}$s may be the same or different, or a pharmaceutically acceptable salt thereof.

17. A method for modulating a $S1P_5$ receptor according to claim 16, wherein the compound is represented by the following general formula (I):

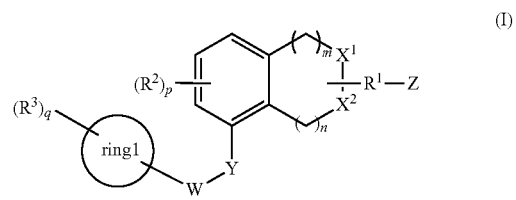

wherein, W represents (1) a C1-6 alkylene group, (2) a C2-6 alkenylene group, (3) a C2-6 alkynylene group, (4) a —C1-6 alkylene-O—, (5) a —C2-6 alkenylene-O—, (6) a —C2-6 alkynylene-O— or (7) a —C1-6 alkylene-ring2-, $R^3$ represents (1) a halogen atom, (2) a C1-4 alkyl group, (3) a C1-4 haloalkyl group, (4) a C1-4 alkoxy group, (5) a C1-4 haloalkoxy group, (6) a nitrile group, (7) a —S—C1-4 alkyl group, or (8) a —S—C1-4 haloalkyl group, provided that the C1-4 alkyl group or the C1-4 haloalkyl group represented by $R^3$ is branched chain, C1-2 alkyl groups branched from the same carbon atom may be taken together with a carbon atom to which they are bound, to form a C3-4 saturated carbocyclic ring, when q is 2 or more, a plurality of $R^3$s may be the same or different and other symbols have the same meanings as described in claim 16.

* * * * *

UNITED STATES PATENT AND TRADEMARK OFFICE
CERTIFICATE OF CORRECTION

PATENT NO. : 10,730,830 B2
APPLICATION NO. : 16/073620
DATED : August 4, 2020
INVENTOR(S) : Toshihide Watanabe, Kensuke Kusumi and Yuichi Inagaki It is certified that error appears in the above-identified patent and that said Letters Patent is hereby corrected as shown below:

On the Title Page

ABSTRACT, delete " 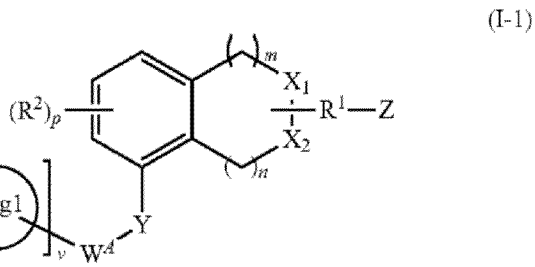 " and insert

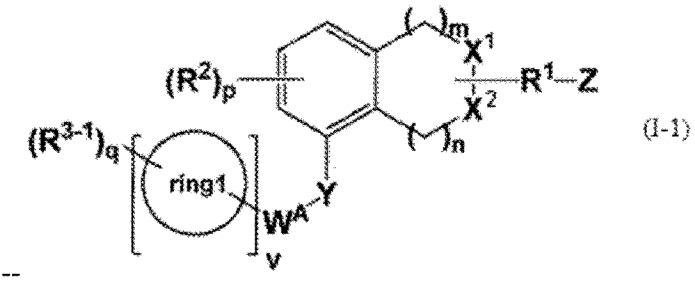

-- therefor;

In the Specification

Technical Field, Column 1, Line 15, delete " 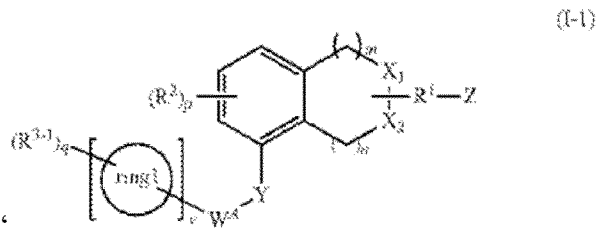 " and

Signed and Sealed this
Fifth Day of January, 2021

Andrei Iancu
*Director of the United States Patent and Trademark Office*

CERTIFICATE OF CORRECTION (continued)
U.S. Pat. No. 10,730,830 B2 insert -- 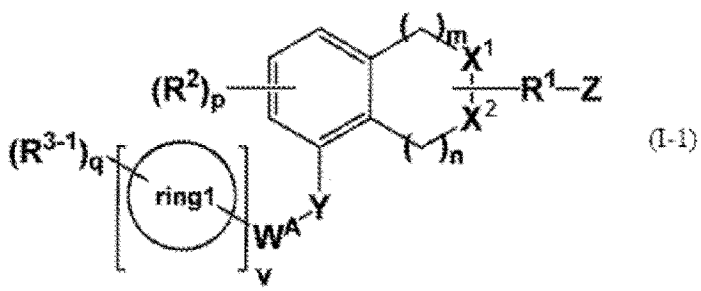 -- therefor;

Summary of the Invention, Column 4, Line 10, delete

" 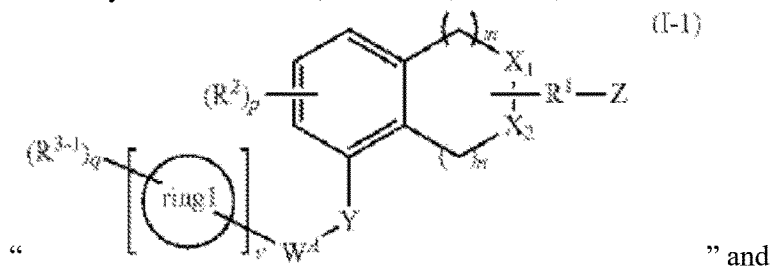 " and insert

-- 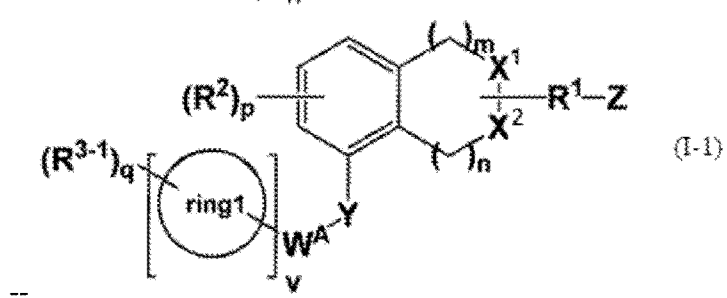 -- therefor;

In the Claims

In Claim 1, Column 57, Line 58, delete

" 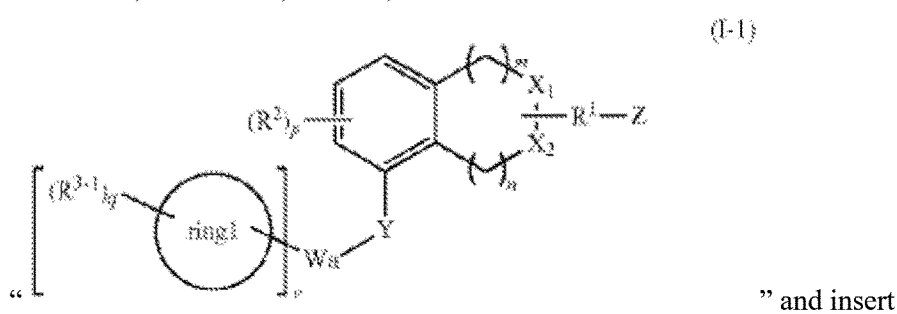 " and insert

CERTIFICATE OF CORRECTION (continued)
U.S. Pat. No. 10,730,830 B2

Page 3 of 4

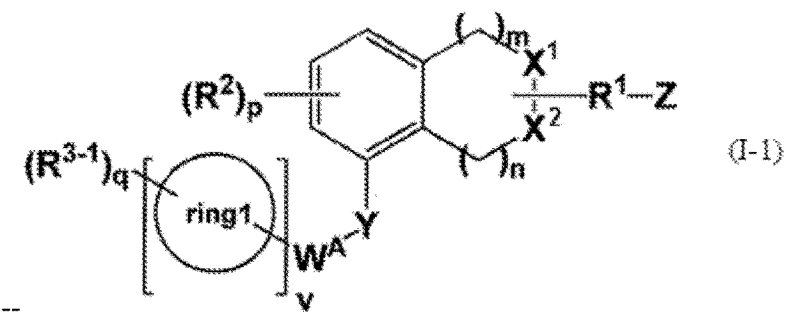

-- 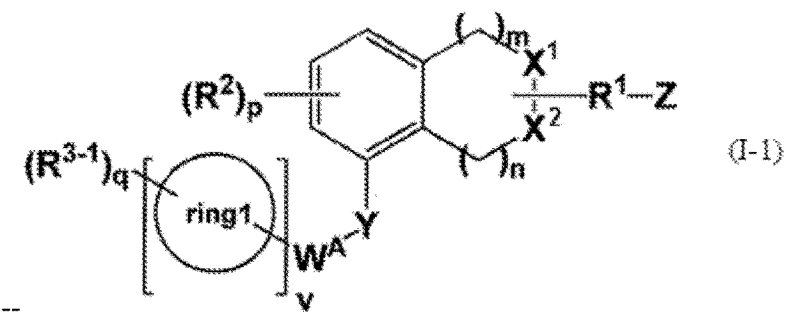 -- therefor;

In Claim 2, Column 59, Line 5, delete " 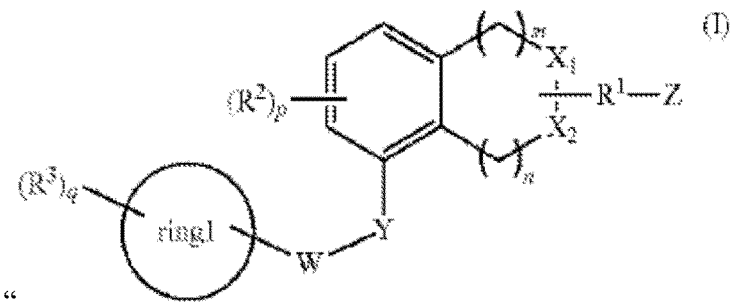 "

and insert -- 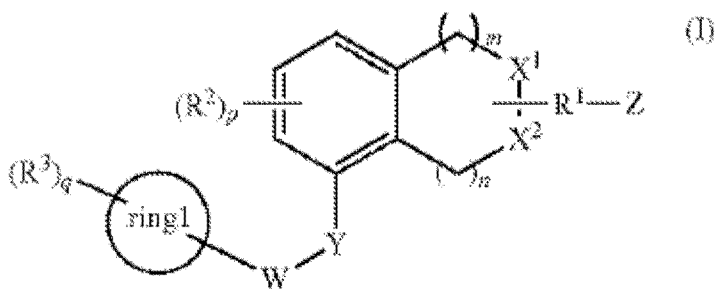 -- therefor;

In Claim 6, Column 59, Line 43, after "comprising", insert --:--;

In Claim 7, Column 59, Line 55, delete

" 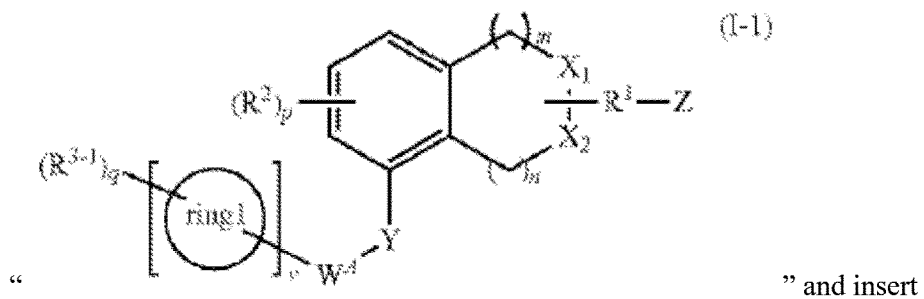 " and insert

CERTIFICATE OF CORRECTION (continued)
U.S. Pat. No. 10,730,830 B2

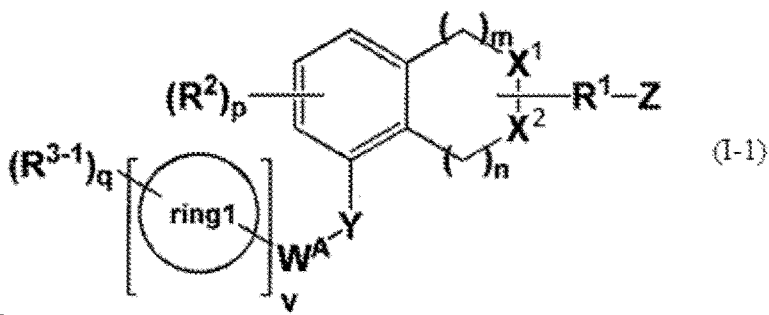

-- -- therefor;

In Claim 7, Column 60, Line 50, after "represents", delete "(1)";

In Claim 13, Column 61, Line 28, delete "(I);" and insert --(I):-- therefor;

In Claim 16, Column 62, Line 10, delete

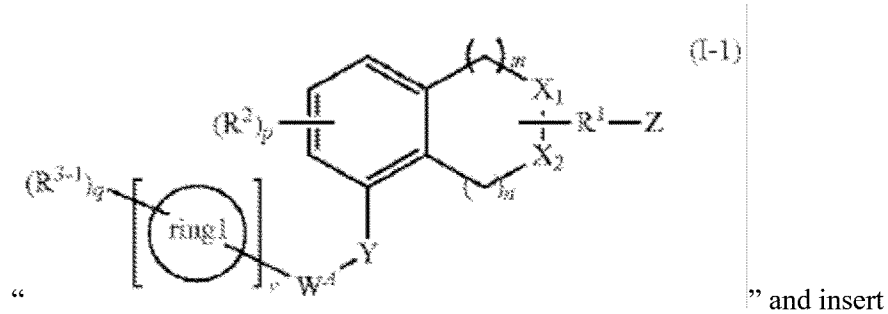

" " and insert

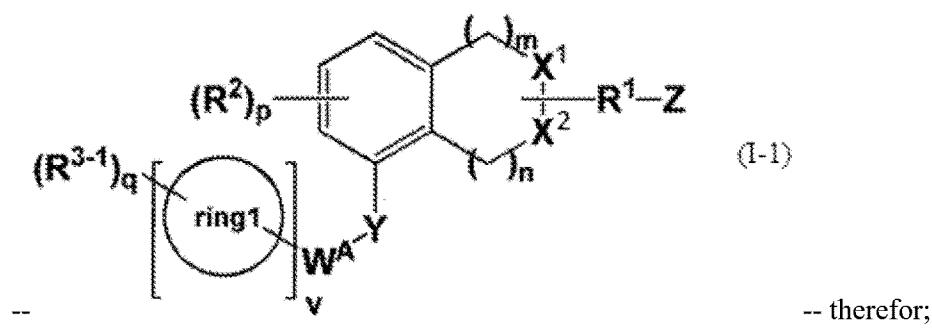

-- -- therefor;

In Claim 16, Column 62, Line 34, delete "alkoxy" and insert --haloalkoxy-- therefor;

In Claim 16, Column 63, Line 7, after "represents", delete "(1)".